United States Patent
Liao et al.

(10) Patent No.: US 12,162,944 B2
(45) Date of Patent: Dec. 10, 2024

(54) HUMAN IL-4R BINDING ANTIBODY, ANTIGEN BINDING FRAGMENT THEREOF, AND MEDICAL USE THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Cheng Liao, Lianyungang (CN); Zupeng Xu, Lianyungang (CN); Jiahua Jiang, Lianyungang (CN); Lianshan Zhang, Lianyungang (CN); Xueming Qian, Suzhou (CN); Fei Teng, Suzhou (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 646 days.

(21) Appl. No.: 17/269,449

(22) PCT Filed: Aug. 23, 2019

(86) PCT No.: PCT/CN2019/102169
§ 371 (c)(1),
(2) Date: Feb. 18, 2021

(87) PCT Pub. No.: WO2020/038454
PCT Pub. Date: Feb. 27, 2020

(65) Prior Publication Data
US 2021/0238294 A1 Aug. 5, 2021

(30) Foreign Application Priority Data

Aug. 24, 2018 (CN) .................. 201810971269.2
Dec. 4, 2018 (CN) .................. 201811472752.2
Mar. 22, 2019 (CN) .................. 201910221311.3
May 15, 2019 (CN) .................. 201910401923.0

(51) Int. Cl.
*C07K 16/28* (2006.01)
*A61K 39/00* (2006.01)

(52) U.S. Cl.
CPC .... *C07K 16/2866* (2013.01); *A61K 2039/505* (2013.01); *C07K 2317/565* (2013.01); *C07K 2317/567* (2013.01)

(58) Field of Classification Search
CPC .......... C07K 16/2866; C07K 2317/565; C07K 2317/567; C07K 2317/24; A61K 2039/505
See application file for complete search history.

(56) References Cited

U.S. PATENT DOCUMENTS 9,676,850 B2 * 6/2017 Saunders et al. ...... C07K 16/28

FOREIGN PATENT DOCUMENTS

| CN | 108373505 A | 8/2018 |
|---|---|---|
| CN | 108409860 A | 8/2018 |
| EP | 3064511 A1 | 9/2016 |
| WO | 2001092340 A2 | 12/2001 |
| WO | 2008054606 A2 | 5/2008 |
| WO | 2010053751 A1 | 5/2010 |
| WO | 2014031610 A1 | 2/2014 |

OTHER PUBLICATIONS

Gooderham et al., Dupilumab: A review of its use in the treatment of atopic dermatitis, 2018, J Am Acad Dermatol 78:S28-36 (Year: 2018).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Greenspan et al. 1999 Defining epitopes: It's not as easy as it seems; Nature Biotechnology, 17:936-937 (Year: 1999).*
Bork. Powers and Pitfalls in Sequence Analysis: The 70% Hurdle. Genome Research, 2000, 10:398-400 (Year: 2000).*
Sicherer et al., J Allergy Clin Immunol 2010; 125: S116-25 (Year: 2010).*
Brooten-Brooks, VeryWellHealth, 2021, verywellhealth.com/are-allergies-hereditary-5198808?print) (Year: 2021).*
Aldakheel, Int. J. Environ. Res. Public Health 2021, 18, 12105, 29 pages (Year: 2021).*
Yang Guangyong et al., "Construction and Panning of scFv Phage Display Library Against Recombinant Interleukin 4 Receptor," Chinese Journal of Cellular and Molecular Immunology, vol. 32, No. (6), Dec. 31, 2016 (Dec. 31, 2016), pp. 829-833.

(Continued)

*Primary Examiner* — Vanessa L. Ford
*Assistant Examiner* — Danaya L Middleton
(74) *Attorney, Agent, or Firm* — MORGAN, LEWIS & BOCKIUS LLP

(57) ABSTRACT

The present disclosure relates to a human IL-4R binding antibody, an antigen binding fragment thereof, and a medical use thereof. Provided are a chimeric antibody and a humanized antibody, including a CDR region from a human IL-4R binding antibody and an antigen binding fragment thereof, a pharmaceutical composition including the human IL-4R binding antibody and the antigen binding fragment thereof, and a use thereof as a drug treating allergic disease. Also provided is a use of the humanized antibody IL-4R binding antibody in preparing a drug used for treating IL-4R mediated diseases or illnesses.

18 Claims, 1 Drawing Sheet
Specification includes a Sequence Listing.

(56) References Cited

OTHER PUBLICATIONS

Namita A. Gandhi et al., Targeting key proximal drivers of type 2 inflammation in disease, Nature Reviews Drug Discovery, Oct. 16, 2015, vol. 15, No. 1, pp. 35-50 (16 pages). doi: 10.1038/nrd4624. Epub Oct. 16, 2015. PMID: 26471366.
Dupixent Highlights of Prescribing Information, sanofi-aventis U.S. LLC (Bridgewater, NJ 08807) and Regeneron Pharmaceuticals, Inc. (Tarrytown, NY 10591), Dupixent® is a registered trademark of Sanofi Biotechnology, © 2023 Regeneron Pharmaceuticals, Inc. (54 pages).

* cited by examiner

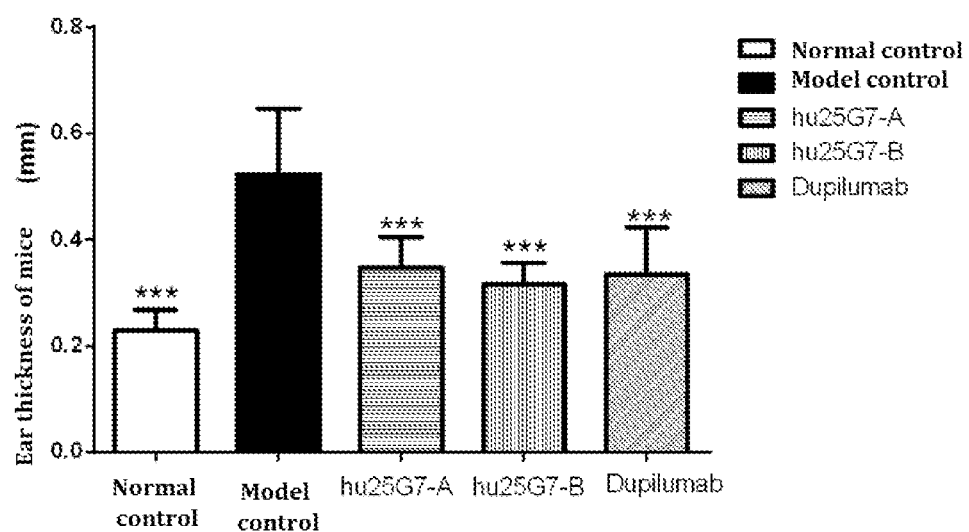

HUMAN IL-4R BINDING ANTIBODY, ANTIGEN BINDING FRAGMENT THEREOF, AND MEDICAL USE THEREOF

CROSS-REFERENCE TO RELATED APPLICATIONS

This application claims the priorities of Chinese application CN201810971269.2 filed on Aug. 24, 2018, Chinese application CN201811472752.2 filed on Dec. 4, 2018, Chinese application CN201910221311.3 filed on Mar. 22, 2019, and Chinese application CN201910401923.0 filed on May 15, 2019. Each of the applications as described above is incorporated herein by reference in its entirety.

FIELD OF THE INVENTION

The present disclosure relates to an antibody that binds to human IL-4R, and antigen-binding fragment thereof. The present disclosure also relates to chimeric antibodies or humanized antibodies comprising CDR regions from the above antibody, and a pharmaceutical composition comprising the antibody that binds to human IL-4R, and antigen-binding fragment thereof, as well as its use as a medicament for treating autoimmune disease.

BACKGROUND OF THE INVENTION

Allergic disease is a serious medical condition, comprising: non-life-threatening allergic reactions, which can be cured over a period of time; and life-threatening allergic diseases.

Current methods for treating allergies include avoiding allergens, pharmacological treatment for symptoms, and prevention with allergen-specific immunotherapy.

Interleukin-4 (IL-4, also known as B cell stimulating factor or BSF-1) has been characterized for its ability to stimulate B cell proliferation in response to low concentration of anti-surface immunoglobulin antibodies. IL-4 has been proven to have a wide range of biological activities, comprising stimulating the growth of T cells, mast cells, granulocytes, megakaryocytes and red blood cells, etc. IL-4 induces the expression of MHC-II in resting B cells, and enhances the secretion of immunoglobulin IgE and IgG1 by activated B cells.

The biological activity of IL-4 is mediated by particular cell surface IL-4 receptors (IL-4Rs). IL-4 receptor (IL-4R) is composed of 802 amino acid residues, and IL-4R is expressed on the surface of T cells, B cells, thymocytes, bone marrow cells, macrophages and mast cells. α chain of IL-4R is also a component of IL-13 receptor (IL-13R), so IL-4R can also mediate the biological activity of IL-13. As a new therapeutic method, a medicament or a composition comprising IL-4R antagonist can be administered to a subject, before, during or after the subject is exposed to allergens or exhibits allergic symptoms.

At present, many pharmaceutical companies in various countries are developing monoclonal antibodies against IL-4R for the treatment of various related allergic diseases. Related patent applications include, for example, WO2010053751, WO2001092340, WO2008054606, WO2014031610, etc. Among them, Dupilumab, an asthma medication which was developed by Sanofi Regeneron, has been approved for marketing for dermatitis indications. For asthma indications, phase III clinical trials have also been completed, and entered the marketing approval stage.

The existing treatment strategies are not effective or have greater risks. Therefore, there is still a need in the art to provide antibodies that bind to human IL-4R with high selectivity and high biological activity, so as to provide medicament and composition, as well as therapeutic methods that can treat IL-4R-mediated allergic disease by binding to hIL-4R with high affinity and neutralizing the biological activity of IL-4R (comprising blocking the interaction with IL-4R).

SUMMARY OF THE INVENTION

In some embodiments herein, it is provided an antibody that specifically binds to IL-4R (also referred to as an antibody that binds to human IL-4R, an anti-human IL-4R antibody) or antigen-binding fragment thereof, wherein the heavy chain variable region comprises:
(I) HCDR1, HCDR2 and HCDR3 as shown in SEQ ID NO: 3, SEQ ID NO: 4 and SEQ ID NO: 5, respectively; or HCDR variants with 3, 2 or 1 amino acid difference(s) when compared with HCDR1, HCDR2 and HCDR3 as shown in SEQ ID NO: 3, 4 and 5, respectively; or
(II) HCDR1, HCDR2 and HCDR3 as shown in SEQ ID NO: 11, SEQ ID NO: 12 and SEQ ID NO: 13, respectively; or HCDR variants with 3, 2 or 1 amino acid difference(s) when compared with HCDR1, HCDR2 and HCDR3 as shown in SEQ ID NO: 11, 12 and 13, respectively;
and/or, the light chain variable region comprises:
(I) LCDR1, LCDR2 and LCDR3 as shown in SEQ ID NO: 6, SEQ ID NO: 7 and SEQ ID NO: 8, respectively; or LCDR variants with 3, 2 or 1 amino acid difference(s) when compared with LCDR1, LCDR2 and LCDR3 as shown in SEQ ID NO: 6, 7 and 8, respectively; or
(II) LCDR1, LCDR2 and LCDR3 as shown in SEQ ID NO: 14, SEQ ID NO: 15 and SEQ ID NO: 16, respectively; or LCDR variants with 3, 2 or 1 amino acid difference(s) when compared with LCDR1, LCDR2 and LCDR3 as shown in SEQ ID NO: 14, 15 and 16, respectively; or
(III) LCDR1, LCDR2 and LCDR3 as shown in SEQ ID NO: 38, SEQ ID NO: 7 and SEQ ID NO: 40, respectively; or LCDR variants with 3, 2 or 1 amino acid difference(s) when compared with LCDR1, LCDR2 and LCDR3 as shown in SEQ ID NO: 38, 7 and 40, respectively; or
(IV) LCDR1, LCDR2 and LCDR3 as shown in SEQ ID NO: 42, SEQ ID NO: 39 and SEQ ID NO: 8, respectively; or LCDR variants with 3, 2 or 1 amino acid difference(s) when compared with LCDR1, LCDR2 and LCDR3 as shown in SEQ ID NO: 42, 39 and 8, respectively.

In some embodiments, the antibody that binds to human IL-4R or antigen-binding fragment thereof comprises any one selected from the group consisting of the following (I) to (IV):
(I) a heavy chain variable region, comprising HCDR1, HCDR2 and HCDR3 as shown in SEQ ID NO: 3, SEQ ID NO: 4 and SEQ ID NO: 5, respectively; and a light chain variable region, comprising LCDR1, LCDR2 and LCDR3 as shown in SEQ ID NO: 6, SEQ ID NO: 7 and SEQ ID NO: 8, respectively;
(II) a heavy chain variable region, comprising HCDR1, HCDR2 and HCDR3 as shown in SEQ ID NO: 11, SEQ ID NO: 12 and SEQ ID NO: 13, respectively; and a light chain variable region, comprising LCDR1, LCDR2 and LCDR3 as shown in SEQ ID NO: 14, SEQ ID NO: 15 and SEQ ID NO: 16, respectively;

(III) a heavy chain variable region, comprising HCDR1, HCDR2 and HCDR3 as shown in SEQ ID NO: 3, SEQ ID NO: 4 and SEQ ID NO: 5, respectively; and a light chain variable region, comprising LCDR1, LCDR2 and LCDR3 as shown in SEQ ID NO: 38, SEQ ID NO: 7 and SEQ ID NO: 40, respectively; and (IV) a heavy chain variable region, comprising HCDR1, HCDR2 and HCDR3 as shown in SEQ ID NO: 3, SEQ ID NO: 4 and SEQ ID NO: 5 respectively; and a light chain variable region, comprising LCDR1, LCDR2 and LCDR3 as shown in SEQ ID NO: 42, SEQ ID NO: 39 and SEQ ID NO: 8, respectively.

In some embodiments of the antibody that binds to human IL-4R or antigen-binding fragment thereof, the heavy chain variable region comprises:

(I) a sequence as shown in SEQ ID NO: 1 or a sequence having at least 70%, 80%, 90%, 95%, 98%, 99% identity to SEQ ID NO:1; or (II) a sequence as shown in SEQ ID NO: 9 or a sequence having at least 70%, 80%, 90%, 95%, 98%, 99% identity to SEQ ID NO: 9; or (III) a sequence as shown in SEQ ID NO: 43 or a sequence having at least 70%, 80%, 90%, 95%, 98%, 99% identity to SEQ ID NO: 43;

and/or, the light chain variable region comprises:

(I) a sequence as shown in SEQ ID NO:2 or a sequence having at least 70%, 80%, 90%, 95%, 98%, 99% identity to SEQ ID NO:2; or (II) a sequence as shown in SEQ ID NO: 10 or a sequence having at least 70%, 80%, 90%, 95%, 98%, 99% identity to SEQ ID NO: 10; or (III) a sequence as shown in SEQ ID NO: 37 or a sequence having at least 70%, 80%, 90%, 95%, 98%, 99% identity to SEQ ID NO:37; or (IV) a sequence as shown in SEQ ID NO: 41 or a sequence having at least 70%, 80%, 90%, 95%, 98%, 99% identity to SEQ ID NO:41.

In at least one embodiment of the antibody that binds to human IL-4R or antigen-binding fragment thereof, wherein:

the heavy chain variable region is as shown in SEQ ID NO: 1 and the light chain variable region is as shown in SEQ ID NO: 2; or the heavy chain variable region is as shown in SEQ ID NO: 9 and the light chain variable region is as shown in SEQ ID NO: 10; or the heavy chain variable region is as shown in SEQ ID NO: 43, and the light chain variable region is as shown in SEQ ID NO: 37; or the heavy chain variable region is as shown in SEQ ID NO: 43, and the light chain variable region is as shown in SEQ ID NO: 41.

In some embodiments of the antibody that binds to human IL-4R or antigen-binding fragment thereof, wherein:

the heavy chain variable region comprises:

(I) a sequence as shown in one of SEQ ID NOs: 25-27 or a sequence having at least 70%, 80%, 90% identity to one of SEQ ID NOs: 25-27; or (II) a sequence as shown in one of SEQ ID NOs: 31-33 or a sequence having at least 70%, 80%, 90% identity to one of SEQ ID NOs: 31-33;

and/or the light chain variable region comprises:

(I) a sequence as shown in one of SEQ ID NOs: 28-30 or a sequence having at least 70%, 80%, 90% identity to one of SEQ ID NOs: 28-30; or (II) a sequence as shown in one of SEQ ID NOs: 34-36 or a sequence having at least 70%, 80%, 90% identity to one of SEQ ID NOs: 34-36.

In some particular embodiments, the heavy chain variable region is as shown in one of SEQ ID NOs: 25-27, and the light chain variable region is as shown in one of SEQ ID NOs: 28-30.

In other particular embodiments, the heavy chain variable region is as shown in one of SEQ ID NOs: 31-33, and the light chain variable region is as shown in one of SEQ ID NOs: 34-36.

In some embodiments, the heavy chain of the antibody that binds to human IL-4R or antigen-binding fragment thereof comprises:

(I) a sequence as shown in SEQ ID NO:17 or a sequence having at least 70%, 80%, 90% identity to SEQ ID NO:17; or (II) a sequence as shown in SEQ ID NO: 19 or a sequence having at least 70%, 80%, 90% identity to SEQ ID NO: 19; or (III) a sequence as shown in SEQ ID NO: 44 or a sequence having at least 70%, 80%, 90% identity to SEQ ID NO: 44.

In some embodiments, the light chain of the antibody that binds to human IL-4R or antigen-binding fragment thereof comprises:

(I) a sequence as shown in SEQ ID NO:18 or a sequence having at least 70%, 80%, 90% identity to SEQ ID NO:18; or (II) a sequence as shown in SEQ ID NO: 20 or a sequence having at least 70%, 80%, 90% identity to SEQ ID NO: 20; or (III) a sequence as shown in SEQ ID NO: 45 or a sequence having at least 90% identity to SEQ ID NO: 45; or (IV) a sequence as shown in SEQ ID NO: 46 or a sequence having at least 90% identity to SEQ ID NO: 46.

In at least one embodiment, the heavy chain is as shown in SEQ ID NO: 17 and the light chain is as shown in SEQ ID NO: 18.

In another embodiment, the heavy chain is as shown in SEQ ID NO: 19 and the light chain is as shown in SEQ ID NO: 20.

In another embodiment, the heavy chain is as shown in SEQ ID NO: 44 and the light chain is as shown in SEQ ID NO: 45.

In another embodiment, the heavy chain is as shown in SEQ ID NO: 44 and the light chain is as shown in SEQ ID NO: 46.

In some embodiments, the anti-IL-4R antibody or antigen-binding fragment is murine antibody, chimeric antibody, human antibody, humanized antibody or fragment thereof.

In some particular embodiments, the anti-IL-4R antibody or antigen-binding fragment is humanized.

In some embodiments, the anti-IL-4R antibody or antigen-binding fragment thereof comprises a fragment or combination thereof selected from the group consisting of the following:

FR region sequence derived from human germline light chain IGKV3-11*01;

back mutation sequence having at least 95% identity to FR region derived from human germline light chain IGKV3-11*01. In some particular embodiments, the back mutation is any one selected from the group consisting of L46P, L47W and F71Y, or the combination thereof.

In some embodiments, the anti-IL-4R antibody or antigen-binding fragment thereof comprises a fragment or combination thereof selected from the group consisting of the following:
FR region sequence derived from human germline heavy chain IGHV3-48*01;
back mutation sequence having at least 95% identity to FR region derived from human germline heavy chain IGHV3-48*01. In some particular embodiments, the back mutation is any one selected from the group consisting of S49A, F67S and A93T, or the combination thereof.

In some embodiments, the anti-IL-4R antibody or antigen-binding fragment thereof comprises a fragment or combination thereof selected from the group consisting of the following:
FR region sequence derived from human germline light chain IGKV2D-29*01;
back mutation sequence having at least 95% identity to FR region derived from human germline light chain IGKV2D-29*01. In some particular embodiments, the back mutation is selected from the group consisting of M4L and/or V58I.

In some embodiments, the anti-IL-4R antibody or antigen-binding fragment thereof further comprises a fragment or combination thereof selected from the group consisting of:
FR region sequence derived from human germline heavy chain IGHV1-2*02;
back mutation sequence having at least 95% identity to FR region derived from human germline heavy chain IGHV1-2*02. In some particular embodiments, the back mutation is any one selected from the group consisting of M69L, R71I, T73K and R94K, or the combination thereof.

In some embodiments, the heavy chain variable region of the anti-IL-4R antibody or antigen-binding fragment thereof comprises heavy chain framework regions of human IgG1, IgG2, IgG3 or IgG4 or variants thereof. In some particular embodiments, the heavy chain variable region comprises heavy chain framework regions of human IgG1 or variants thereof, for example, the heavy chain variable region as shown in SEQ ID NO: 43 or heavy chain variable region variant having at least 85% sequence identity to SEQ ID NO: 43.

In some embodiments, the anti-IL-4R antibody or antigen-binding fragment thereof comprises constant region(s) of human κ, λ chain or variants thereof, for example, the light chain variable region as shown in SEQ ID NO: 44 or light chain variable region variant having at least 85% sequence identity to SEQ ID NO: 44.

In some embodiments, the humanized IL-4R antibody or fragment thereof as described above further comprises heavy chain constant region(s) of human IgG1, IgG2, IgG3 or IgG4 or variants thereof.

In at least one embodiment, the antibody comprises heavy chain constant region(s) of human IgG2 or IgG4. IgG2 or IgG4 has no ADCC toxicity. Alternatively, IgG1 without ADCC (antibody-dependent cell-mediated cytotoxicity) toxicity after amino acid mutation can be used.

In at least one embodiment, the variant comprises heavy chain constant region mutation(s) selected from the group consisting of: mutation(s) that reduces the ADCC function, or causes loss of ADCC function, such as but not limited to N297A, L234A, L235A in IgG1.

In some embodiments of the anti-IL-4R antibody or antigen-binding fragment thereof, wherein the antibody is a humanized antibody, and the heavy chain sequence is as shown in SEQ ID NO: 17 or has at least 85% sequence identity to SEQ ID NO: 17; the light chain sequence is as shown in SEQ ID NO: 18 or has at least 85% sequence identity to SEQ ID NO: 18.

In some embodiments of the anti-IL-4R antibody or antigen-binding fragment thereof, wherein the antibody is a humanized antibody, and the heavy chain sequence is as shown in SEQ ID NO: 19 or has at least 85% sequence identity to SEQ ID NO: 19; the light chain sequence is as shown in SEQ ID NO: 20 or has at least 85% sequence identity to SEQ ID NO: 20.

In some embodiments of the anti-IL-4R antibody or antigen-binding fragment thereof, wherein the antibody is a humanized antibody, and the heavy chain sequence is as shown in SEQ ID NO: 44 or has at least 85% sequence identity to SEQ ID NO: 44; the light chain sequence is as shown in SEQ ID NO: 45 or has at least 85% sequence identity to SEQ ID NO: 45.

In some embodiments of the anti-IL-4R antibody or antigen-binding fragment thereof, wherein the antibody is a humanized antibody, and the heavy chain sequence is as shown in SEQ ID NO: 44 or has at least 85% sequence identity to SEQ ID NO: 44; the light chain sequence is as shown in SEQ ID NO: 46 or has at least 85% sequence identity to SEQ ID NO: 46.

In some embodiments, it is provided an isolated anti-IL-4R antibody or antigen-binding fragment thereof, which is characterized in that it competes for binding to human IL-4R with any antibody that binds to human IL-4R or antigen-binding fragment thereof as described above.

In some embodiments, it is provided a bi-specific antibody or a multi-specific antibody, which comprises the light chain variable region and/or heavy chain variable region of the antibody that binds to human IL-4R or antigen-binding fragment thereof according to the present application.

In other embodiments, it is provided a single chain antibody which comprises the light chain variable region and/or heavy chain variable region of the antibody that binds to human IL-4R or antigen-binding fragment thereof according to the present application.

In some embodiments, it is provided a polynucleotide, which encodes the antibody that binds to human IL-4R or antigen-binding fragment thereof according to the present application.

In other embodiments, it is provided a polynucleotide, which encodes an antibody that competitively binds to IL-4R or epitope thereof with the antibody that binds to human IL-4R or the antigen-binding fragment thereof according to the present application.

In other embodiments, it is provided a polynucleotide, which encodes the bi-specific antibody, multi-specific antibody, or single chain antibody as described above.

In some embodiments, the polynucleotide according to the present application is DNA or RNA.

In some embodiments, it is provided a vector comprising the polynucleotide as described above, which is a eukaryotic expression vector, a prokaryotic expression vector or a viral vector.

In some embodiments, it is provided a host cell, which is transformed with the vector as described above, and the host cell is selected from the group consisting of a prokaryotic cell or a eukaryotic cell.

In at least one embodiment, the prokaryotic cell is selected from bacteria, such as *E. coli*.

In at least one embodiment, the eukaryotic cell is selected from the group consisting of yeast and mammalian cells, such as *Pichia pastoris* or CHO cells.

In some embodiments, it is provided a method for detecting or measuring IL-4R, the method comprising the step of contacting a sample with the anti-IL-4R antibody or antigen-binding fragment thereof as described above.

In some embodiments, it is provided a reagent for detecting or measuring human IL-4R, and the reagent comprises the anti-IL-4R antibody or antigen-binding fragment thereof as described above.

In some embodiments, it is provided a reagent for detecting or measuring human IL-4R, the reagent comprising an antibody that competitively binds to IL-4R or epitope thereof with the antibody that binds to human IL-4R or antigen-binding fragment thereof according to the present application.

In some embodiments, it is provided a reagent for detecting or measuring human IL-4R, the reagent comprising bi-specific antibody, multi-specific antibody, and single chain antibody as described above.

In some embodiments, it is provided a diagnostic agent for diagnosing disease related to human IL-4R-positive cell, the diagnostic agent comprising said anti-IL-4R antibody or antigen-binding fragment thereof as described above. In other embodiments, the diagnostic agent comprises an antibody that competitively binds to IL-4R or epitope thereof with the antibody that binds to human IL-4R or antigen-binding fragment thereof according to the present application.

In some embodiments, it is provided a pharmaceutical composition, which comprises:
the antibody that binds to human IL-4R or antigen-binding fragment thereof according to the present application, and
a pharmaceutically acceptable excipient, diluent or carrier.

In some particular embodiments, the dose unit of the pharmaceutical composition comprises 1 mg to 1000 mg of the IL-4R antibody or antigen-binding fragment thereof according to the present application.

In some particular embodiments, the concentration of the IL-4R antibody or antigen-binding fragment thereof comprised in the pharmaceutical composition is from 1 mg/L to 1000 mg/L.

In some particular embodiments, the pharmaceutical composition comprises buffer, the content of buffer is from 1 mM to 1000 mM.

In some embodiments, it is provided use of the antibody that binds to human IL-4R or antigen-binding fragment thereof as described above in the preparation of a medicament for treating or preventing IL-4R-mediated disease or condition.

In some embodiments, it is provided use of the pharmaceutical composition as described above in the preparation of a medicament for treating or preventing IL-4R-mediated disease or condition.

In some embodiments, it is provided the antibody that binds to human IL-4R or antigen-binding fragment thereof as described above for use in treating or preventing disease or condition.

In some embodiments, it is provided the pharmaceutical composition described above for use in the treatment or prevention of disease or condition.

In the context of present application, the condition or disease may be an immune disease or condition.

In some embodiments, the disease or condition is selected from the group consisting of: asthma, nasal polyps, chronic sinusitis, allergic skin disease, eosinophilic esophagitis, chronic obstructive pulmonary disease, allergic rhinitis, arthritis, inflammatory disease, allergic reaction, autoimmune lymphoproliferative syndrome, autoimmune hemolytic anemia, Barrett's esophagus, autoimmune uveitis, tuberculosis and nephropathy.

In at least one embodiment, the disease or condition is asthma.

In other embodiments, the disease or condition is allergic skin disease.

In some embodiments, it is provided an antibody that binds to human IL-4R or antigen-binding fragment thereof, wherein said antigen-binding fragment is Fab, Fv, scFv or F(ab')2.

In some embodiments, it is provided a method for treating and/or preventing IL-4R-mediated disease or condition, the method comprising: administering a therapeutically effective amount (or a prophylactically effective amount) of the antibody that binds to human IL-4R or antigen-binding fragment thereof as described above, to a patient (or subject) in need thereof.

In some embodiments, it is provided a method for treating and/or preventing IL-4R-mediated disease or condition, the method comprising: administering a therapeutically effective amount (or a prophylactically effective amount) pharmaceutical composition as described above, to a patient (or subject) in need thereof. In some embodiments, it is provided a method for treating and/or preventing immune disease, comprising administering a therapeutically effective amount (or a prophylactically effective amount) of the antibody that binds to human IL-4R or antigen-binding fragment thereof or the pharmaceutical composition as described above, to a patient (or subject) in need thereof.

Terminology

In order to make the present disclosure being more readily understood, certain technical and scientific terms are specifically defined below. Unless specifically defined elsewhere herein, all other technical and scientific terms used herein have the meaning commonly understood by one of ordinary skill in the art to which present application pertains.

"Human IL-4R (hIL-4R)" means a human cytokine receptor that specifically binds to interleukin-4 (IL-4), IL-4Rα.

As used herein, the three-letter code and the single-letter code for amino acids are as described in J. Biol. Chem, 243, (1968) p 3558.

The term "antibody" refers to immunoglobulin, which is a four-peptide chain structure formed by linking two identical heavy chains and two identical light chains by inter-chain disulfide bonds. Different immunoglobulin heavy chain constant regions exhibit different amino acid compositions and sequence arrangement, thereby presenting different antigenicity. Accordingly, immunoglobulins can be divided into five categories (or referred to as immunoglobulin isotypes), namely IgM, IgD, IgG, IgA and IgE, their heavy chains are u chain, δ chain, y chain, a chain and & chain, respectively. According to the amino acid composition of hinge region as well as the number and location of heavy chain disulfide bonds, the same type of Ig can further be divided into different sub-categories; for example, IgG can be divided into IgG1, IgG2, IgG3, and IgG4. Light chain can be divided into κ or λ chain, considering the different constant regions. Each of the five Igs may have κ or λ chain.

The antibody light chain further comprises a light chain constant region, which comprises a human or murine κ, λ chain or variants thereof.

The antibody heavy chain further comprises a heavy chain constant region, which comprises a human or murine IgG1, IgG2, IgG3, IgG4 or variants thereof.

Near the N-terminus of the antibody heavy chains and light chains sequence, a sequence of about 110 amino acid varies largely, known as the variable region (V region); the rest of the amino acid sequence near the C-terminus is relative stable, known as the constant region (C region). Variable region comprises three hypervariable regions (HVRs) and four framework regions (FRs) having relatively conserved sequence. The three hypervariable regions determine the specificity of the antibody, also known as complementarity determining regions (CDRs). Each light chain variable region (LCVR) and each heavy chain variable region (HCVR) is composed of three CDRs and four FRs, with an order from the amino terminus to the carboxyl terminus being: FR1, CDR1, FR2, CDR2, FR3, CDR3, and FR4. Three light chain CDRs refer to LCDR1, LCDR2, and LCDR3; three heavy chain CDRs refer to HCDR1, HCDR2 and HCDR3.

Antibodies include murine antibodies, chimeric antibodies, humanized antibodies, and human antibodies, which may be obtained by recombination, for example, may be recombinant human antibodies obtained by affinity maturation.

The term "recombinant human antibody" includes human antibodies prepared, expressed, created or isolated by recombinant method, and the techniques and methods involved are well known in the art, such as: (1) antibodies isolated from human immunoglobulin gene transgenic animals or trans-chromosomal animals (e.g., mice), or hybridoma prepared therefrom; (2) antibodies isolated from transformed host cells to express the antibodies, such as transfectoma; (3) antibodies isolated from a recombinant combinatorial human antibody library; and (4) antibodies prepared, expressed, created or isolated by splicing human immunoglobulin gene sequence to another DNA sequences or the like. Such recombinant human antibodies comprise variable region and constant region, such regions involve specific human germline immunoglobulin sequences encoded by germline genes, but also involve subsequent rearrangements and mutations, such as those occur during the antibody maturation.

The term "murine antibody" herein refers to monoclonal antibodies against human IL-4R, which are prepared according to the knowledge and skills in the art. During the preparation, a test object is injected with IL-4R antigen or polypeptide comprising epitope thereof, and then hybridoma expressing the antibody which possesses desired sequence or functional characteristics is separated. In some particular embodiments, the murine IL-4R antibody or antigen-binding fragment thereof further comprises light chain constant region(s) of murine κ, λ chain or variants thereof, or further comprises heavy chain constant region(s) of murine IgG1, IgG2, IgG3 or IgG4, or variants thereof.

The term "human antibody" includes antibodies having variable and constant region(s) from human germline immunoglobulin sequences. Human antibodies of the present application may include amino acid residues that are not encoded by human germline immunoglobulin sequences (e.g., mutations introduced by random or site-specific mutagenesis in vitro or by somatic mutation in vivo). However, the term "human antibody" does not include an antibody in which CDR sequences derived from other mammalian species (such as mouse) germline have been grafted onto human framework sequence (i.e., "humanized antibody").

The term "humanized antibody", also known as CDR-grafted antibody, refers to antibodies generated by grafting non-human species CDR sequences onto variable region framework of human antibody. Humanized antibodies overcome the strong antibody response induced by chimeric antibodies which carry a large amount of heterogeneous protein components. To avoid a decrease of activity along with the decrease of immunogenicity, the variable region of the human antibody would be subjected to a minimum back mutation to maintain the activity.

The term "chimeric antibody", is an antibody which is formed by fusing the variable region of a murine antibody with the constant region of a human antibody, the chimeric antibody can alleviate the murine antibody-induced immune response. To establish a chimeric antibody, hybridoma secreting specific murine monoclonal antibody is firstly established, a variable region gene is then cloned from mouse hybridoma cells, then a constant region gene of a human antibody is cloned as desired, the mouse variable region gene is ligated to the human constant region gene to form a chimeric gene which can be inserted into a human vector, and finally the chimeric antibody molecule is expressed in an eukaryotic or prokaryotic industrial system. The constant region of a human antibody is selected from heavy chain constant region(s) of human IgG1, IgG2, IgG3 or IgG4 or variants thereof, preferably heavy chain constant region(s) of human IgG2 or IgG4, or IgG1 which has no ADCC (antibody-dependent cell-mediated cytotoxicity) after amino acid mutation.

"Antigen-binding fragment" refers to a Fab fragment, a Fab' fragment, a F(ab')2 fragment having antigen-binding activity, a Fv fragment, scFv fragment binding to human IL-4R, as well as polypeptide or protein comprising the fragments above. Said "antigen-binding fragment" comprises one or more CDRs of the antibody according to present application. Fv fragment is a minimum antibody fragment carrying all antigen-binding sites, it comprises a heavy chain variable region and a light chain variable region, but without constant region. Generally, Fv antibody further comprises a polypeptide linker between the VH and VL domains, and is capable of forming a structure necessary for antigen binding. Also, different linkers can be used to connect the variable regions of two antibodies to form a polypeptide chain, namely single chain antibody or single chain Fv (scFv).

"Binding to IL-4R", refers to the ability to interact with human IL-4R. The term "antigen binding site" as used herein refers to three-dimensional sites recognized by the antibody or the antigen-binding fragment of the present application.

The term "epitope" refers to the sites on an antigen that specifically bind to an immunoglobulin or antibody. The epitope can be formed by adjacent amino acids, or by non-adjacent amino acids which have been brought to be closer due to tertiary folding of a protein. The epitope formed by adjacent amino acids is typically retained after exposure to denaturing solvent, whereas the epitope formed by tertiary folding is typically absent after treatment with denaturing solvent. Epitopes typically include at least 3-15 amino acids in a unique spatial conformation. Methods for determining epitope bound by a given antibody are well known in the art, comprising immuno-blotting and immuno-precipitation assay, and the like. Methods for determining the spatial conformation of an epitope include techniques in the art and techniques described herein, such as X-ray crystallography and two-dimensional nuclear magnetic resonance, and the like.

The terms "specifically binds to" and "selectively binds to", refer to the binding of an antibody to an epitope on a predetermined antigen. Typically, the antibody binds to a predetermined antigen with an equilibrium dissociation constant ($K_D$) of approximately less than $10^{-7}$ M or even less, and the affinity of the antibody for binding to the predetermined antigen is at least two times higher than that for binding to non-specific antigens (such as BSA) other than the predetermined antigen or closely-related antigens, as measured in an instrument via surface plasmon resonance (SPR) technique, wherein the recombinant human IL-4R is used as an analyte while the antibody is used as a ligand. The term "an antibody recognizing an antigen" can be used interchangeably herein with the term "an antibody specifically binding to".

The term "cross-reaction" refers to the ability of the antibody of the present application to bind to IL-4R from different species. For example, an antibody of the present application that binds to human IL-4R can also bind to IL-4R from another species. Cross-reactivity is measured by detecting the specific reactivity with purified antigen in binding assays (e.g., SPR and ELISA), or by detecting the binding or functional interaction with cells physiologically expressing IL-4R. Methods for determining cross-reactivity include standard binding assays as described herein, such as surface plasmon resonance analysis (SPR), or flow cytometry.

The term "neutralizing" or "blocking" antibody refers to an antibody which binds to hIL-4R and leads to the inhibition of biological activity of hIL-4 and/or hIL-3. This inhibition of hIL-4 and/or IL-13 biological activity can be evaluated by measuring one or more indicators of hIL-4/or hIL-13 biological activity well known in the art, such as hIL-4 and/or hIL-13-induced cell activation and the binding of hIL-4 to hIL-4R, for example, those in CN103739711A. "Inhibition of growth" (e.g., when referred to cells) is intended to include any measurable decrease in cell growth.

The terms "inducing immune response" and "enhancing immune response" are used interchangeably and refer to the immune response to the stimulation of a particular antigen (i.e., passive or adaptive). The term "inducing", with respect to CDC or ADCC, refers to stimulating a specific mechanism for directly killing cells.

The term "ADCC" (antibody-dependent cell-mediated cytotoxicity) refers to that cells expressing Fc receptor directly kill target cells coated with an antibody through recognizing the Fc segment of the antibody. ADCC effector function of the antibody can be reduced or eliminated via modification on Fc segment of IgG. The modification refers to mutations performed on the antibody heavy chain constant region, such as mutations selected from the group consisting of N297A, L234A and L235A in IgG1, IgG2/4 chimera and F235E or L234A/E235A mutation in IgG4.

Fusion protein is a protein product that is co-expressed by two genes through DNA recombination. Recombinant IL-4R extracellular region Fc fusion protein is a fusion protein obtained by co-expressing IL-4R extracellular region with human antibody Fc fragment, through DNA recombination. The IL-4R extracellular region refers to the part of IL-4R protein expressed outside the cell membrane.

Methods for producing and purifying antibodies and antigen-binding fragments are well known in the art and can be found, for example, in Antibodies, A Laboratory Manual, Cold Spring Harbor, Chapters 5-8 and 15. For example, mice can be immunized with human IL-4R or fragment thereof, and then the resulting antibodies can be renatured, purified and sequenced using conventional methods well known in the art. Antigen-binding fragments can also be prepared by conventional methods. The antibody or antigen-binding fragment described herein is genetically engineered to add one or more human FRs to non-human CDRs. Human FR germline sequences can be obtained from ImMunoGeneTics (IMGT) via website http://imgt.cines.fr, or from The Immunoglobulin FactsBook, 2001ISBN012441351.

The engineered antibody or antigen-binding fragment may be prepared and purified using conventional methods. For example, cDNA sequences encoding a heavy chain and a light chain may be cloned and recombined into GS expression vector. The recombinant immunoglobulin expression vector then may be stably transfected into CHO cells. The sequence of the humanized antibody herein is inserted into a corresponding expression vector by molecular cloning technology, and the corresponding humanized antibody is obtained by expression in HEK293 cell expression system. As a more recommended method in the art, mammalian expression system may result in glycosylation of antibodies, typically at the highly conserved N-terminus in the Fc region. Stable clones may be obtained through expression of an antibody specifically binding to human antigen. Positive clones may be expanded in a serum-free culture medium for antibody production in bioreactors. Culture medium, into which an antibody has been secreted, may be collected and purified by conventional techniques. The antibody may be subjected to filtration and concentration using common techniques. Soluble mixtures and multimers may be effectively removed by common techniques, such as molecular sieve or ion exchange. The obtained product shall be immediately frozen, for example at −70° C., or may be lyophilized.

The antibody may be a monoclonal antibody (mAb), which refers to an antibody obtained from a single cell strain which is but not limited to eukaryotic, prokaryotic, or phage clone cell strain. Monoclonal antibodies and antigen-binding fragment thereof can be obtained, for example, by hybridoma technologies, recombinant technologies, phage display technologies, synthetic technologies (e.g., CDR-grafting), or other technologies known in the art.

Antibodies can be mono-specific, bi-specific or multi-specific antibodies. Multi-specific antibodies show specificity for different epitopes of the target peptide, or may also contain antigen binding domains that show specificity for more than one target peptides. The human anti-IL-4R antibody can be linked to or co-expressed with another functional molecule (such as another peptide or protein). For example, the antibody or fragments thereof can be functionally (e.g. by chemical coupling, gene fusion, non-covalent binding or other means) connected to one or more other molecules (e.g. another antibody or antigen-binding fragment) to produce bi-specific or multi-specific antibody having a second binding specificity.

"Administration", "administering" and "treatment", when applied to an animal, human, experimental subject, cell, tissue, organ, or biological fluid, refers to contacting an exogenous pharmaceutical, therapeutic, diagnostic agent, or composition with the animal, human, subject, cell, tissue, organ, or biological fluid. "Administration", "administering" and "treatment" can refer to such as therapeutic, pharmacokinetic, diagnostic, research and experimental methods. Treatment of a cell involves contacting a reagent with a cell, as well as contacting a reagent with a fluid wherein said fluid is in contact with the cell. "Administration", "administering" and "treatment" also mean in vitro and ex vivo treatment of e.g. a cell, by using a reagent, diagnostic, binding composition, or by using another cell. "Treatment" when applied to a human, veterinary or a research subject, refers to therapeutic treatment, prophylactic or preventative measures, research as well as diagnostic applications.

"To treat" means internally or externally administration of a therapeutic agent (such as a composition comprising any of the antibodies or antigen-binding fragment thereof of the present application) to a patient (or subject) having, suspected to have or susceptible to one or more disease symptoms for which the agent has known therapeutic activity. Typically, the therapeutic agent is administered in an amount effective to alleviate one or more disease symptoms in the treated patient (or subject) or population, either by inducing the regression of such symptom(s), or by inhibiting the progression of such symptom(s) to any clinically measurable degree. The amount of a therapeutic agent that is effective to alleviate any particular disease symptom (also referred to "therapeutically effective amount") may vary according to factors such as the disease state, age, and weight of the patient (or subject), and the ability of the medicament to elicit a desired effect in the patient (or subject). Whether a disease symptom has been alleviated can be assessed by any clinical measurement typically used by physicians or other skilled healthcare providers to assess the severity or progression status of that symptom. While one embodiment of the present application (e.g., a treatment method or article of manufacture) may not be effective in alleviating the disease symptom(s) of interest in each patient (or subject), it should alleviate the target disease symptom(s) of interest in a statistically significant number of patient (or subject) as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Conservative modification" or "conservative replacement or substitution" means the substitution of other amino acids showing similar characteristics (such as charge, side chain size, hydrophobicity/hydrophilicity, main chain conformation and rigidity, etc) for the amino acids in a protein, such that the modification can be frequently performed without changing the biological activity of the protein. Those skilled in the art know that, generally, a single amino acid substitution in a non-essential region of a polypeptide does not substantially change the biological activity (see for example, Watson et al. (1987) Molecular Biology of the Gene, The Benjamin/Cummings Pub. Co., Page 224 (4th edition)). In addition, the substitution of amino acids with similar structure or function is unlikely to disrupt biological activity.

"Effective amount" involves an amount sufficiently to ameliorate or prevent a symptom or sign of a medical condition. Effective amount also means an amount sufficiently to allow or facilitate diagnosis. An effective amount for a particular subject or veterinary subject may vary depending on factors such as the condition being treated, the general health of the subject, the route and dose of administration and the severity of side effects. An effective amount can be the maximal dose or dosing protocol that avoids significant side effects or toxic effects.

"Exogenous" refers to substances that are produced outside an organism, cell, or human body, depending on the context.

"Endogenous" refers to substances that are produced within a cell, organism, or human body, depending on the context.

"Homology" or "identity" refers to sequence similarity between two polynucleotide sequences or between two polypeptides. When a position in two sequences to be compared is occupied by the same base or amino acid monomer subunit, e.g., when a position in each of two DNA molecules is occupied by adenine, then the molecules are homologous at this position. The percent of identity between two sequences is a function of the number of matched/homologous positions shared by two sequences divided by the number of positions to be compared, and then multiplied by×100%. For example, if 6 of 10 positions in two sequences are matched or homologous when the sequences are optimally aligned, then the two sequences share 60% identity. Generally, the comparison is made when two sequences are aligned to give maximum percent identity. As used herein, "at least 85% sequence identity" means that the variant has at least 85% homology to the parent sequence, two sequences share at least 85% homology. In some embodiments, having at least 86%, 87%, 88%, 89%, 90%, 91%, 92%, 93%, 94%, 95%, 96%, 97%, 98%, or 99% sequence homology; in some particular embodiments, having 90%, 95% or 99% or higher; in other particular embodiments, having at least 95% sequence homology. The amino acid sequence having at least 85% sequence identity includes one or more amino acid deletions, insertions or substitution mutations when compared with the parent sequence.

As used herein, the expressions "cell" "cell line" and "cell culture" are used interchangeably and all such designations include progeny thereof. Thus, the words "transformant" and "transformed cell" include the primary subject cells and cultures derived therefrom without considering the number of passages. It is also understood that all progeny may not be precisely identical in DNA content, due to deliberate or random mutations. Mutant progeny obtained by screening, which have the same function or biological activity as that of originally transformed cell, are also contemplated.

"Optional" or "optionally" means that the event or situation that follows may occur, but not necessarily occur. The description includes the instances in which the event or circumstance does or does not occur. For example, "optionally comprises 1-3 antibody heavy chain variable region(s)" means that the antibody heavy chain variable region with specific sequence can be, but not necessarily, be present.

"Pharmaceutical composition" refers to a composition comprising a mixture of one or more antibodies or antigen-binding fragment thereof as described herein or a physiologically/pharmaceutically acceptable salt or prodrug thereof along with other chemical components, as well as additional components such as physiologically/pharmaceutically acceptable carriers and excipients. The pharmaceutical composition aims at promoting the administration to an organism, facilitating the absorption of the active ingredient and thereby exerting a biological effect.

DESCRIPTION OF THE DRAWINGS

FIG. 1: In a dermatitis mouse model, after sensitized with acetone, the humanized antibodies hu25G7-A, hu25G7-B and the positive reference antibody Dupilumab were subcutaneously administered twice per week, the ear thickness of mice was measured on day 27. The results show that, compared with the control group, hu25G7-A, hu25G7-B and Dupilumab can effectively reduce the ear thickness of mice, and hu25G7-B shows a better effect than that of Dupilumab.

DETAILED DESCRIPTION OF THE DISCLOSURE

Hereinafter, the present disclosure is further described with reference to the examples. However the scope of the present disclosure is not limited thereto. In the examples, where specific conditions are not described, the experiments are generally conducted under conventional conditions as described in Antibodies, A Laboratory Manual and Molecular Cloning Manual, by Cold Spring Harbor, or under conditions proposed by the material or product manufacturers. Where the source of the reagents is not specifically given, the reagents are commercially available.

Example 1: Immunization of Mice and Testing

His-tagged human IL-4R (h-IL-4R-his) recombinant protein, his-tagged mouse IL-4R (m-IL-4R-his) recombinant protein, and his-tagged rhesus IL-4R (rhesus-IL-4R-his) recombinant protein were synthesized by Acrobiosystems, expressed in HEK293 and purified.

The recombinant protein of human IL-4R with human Fc tag (h-IL-4R-Fc) was designed, expressed and purified in house. The purified protein was used in each of the following experiments in Examples.

The number and position of the CDR amino acid residues in the VL and VH regions of the antibody or antigen-binding fragment in this example comply with the known Kabat numbering system (LCDR1-3, HCDR2-3), or comply with the Kabat and CHOTHIA (ABM) numbering system (HCDR1).

TABLE 1

| | Information of immunogen | |
|---|---|---|
| name | amino acid sequence (from beginning to end) | database no./catalog no. |
| h-IL-4R-his | Met26-His232 | NP_000409.1 |
| m-IL-4R-his | Ile26-Arg233 | NP_001008700 |
| rhesus-IL-4R-his | Met26-Arg232 | G7Q0S7 |
| h-IL-4R-Fc | Met1-His232 | NP_000409.1 |

Anti-human IL4R monoclonal antibodies were produced by immunizing mice. C57BL/6 mice, female, 6-8 week-old (JOINN Laboratories (Suzhou) Research Center Co., Ltd., animal production license number: 201503052) were used in the experiment.

Feeding environment: SPF level. Once the mice were purchased, they were maintained in a laboratory environment for 1 week, adapted to 12/12 hours of light/dark cycle, at temperature 20-25° C.; with humidity 40-60%. The adapted mice were divided into 3 cages, 5 in each cage. The immune antigen was human IL-4R recombinant protein with Fc tag (h-IL4R-Fc, concentration of 0.73 mg/ml). The antigen was emulsified with Freund's adjuvant (sigma, Cat #: F5881): Complete Freund's adjuvant (CFA, Pierce, Cat #77140) was used for the first immunization, and the nucleic acid adjuvant (CpG, Shanghai Sangon) and aluminum adjuvant (Alum, Thermo Cat #77161) was used for the rest of booster immunization.

On Day 0, 70 μg/mouse of emulsified antigen was injected intraperitoneally (IP). On day 14, 28, 42, 56, 77, according to the back mass and abdominal swelling, antigen was injected at back and intraperitoneally (each injection of 0.1 ml). Blood was collected on day 21, 35, 49, 63, and 84 for blood test. ELISA assay was performed on mouse serum according to Test Example 1 to determine the antibody titer in the mouse serum. After the fourth immunization, the mice with high antibody titer in the serum and the titer tending to a plateau were selected for spleen cell fusion; booster immunization was performed 3 days before fusion; antigen solution prepared by using phosphate buffer was intraperitoneally injected at 10 μg/mouse. Using optimized PEG-mediated fusion steps, splenic lymphocytes and myeloma cells Sp2/0 cells (ATCC*CRL-8287™) were fused to obtain hybridomas.

Example 2: ELISA Test and Screening of Antibodies

1. ELISA Binding Test:

ELISA test was used to detect the binding properties of IL-4R antibodies. A microtiter plate directly coated with his-labeled IL-4R recombinant protein was used, the antibody was added to each well, and then the binding activity of the antibody to antigen was detected by adding secondary antibody (HRP-conjugated anti-primary antibody Fc) and HRP substrate TMB.

Human or rhesus IL-4R-his protein was coated onto 96-well microtiter plate, 100 μl per well at a concentration of 0.5 μg/ml, and incubated overnight at 4° C. The plate was washed with washing solution for three times, 250 μl per well. Each washing step was performed with shaking for 10 seconds to ensure sufficient washing. 200 μl/well blocking solution was added and incubated at room temperature for 2 hours. The plate was washed with washing solution for three times, 250 μl per well. Each washing step was performed with shaking for 10 seconds to ensure sufficient washing. 100 μl of anti-IL-4R antibody to be tested diluted with diluent was added to each well, and incubated at room temperature for 1 hour. The plate was washed with washing solution for three times, 250 μl per well. 100 μl of HRP-labeled goat anti-human IgG secondary antibody (diluted at 1:20000 with diluent) was added to each well and incubated at room temperature for 1 hour. The plate was washed with washing solution for three times, 250 μl per well. 100 μl TMB was added to each well and the reaction was maintained for 15 minutes in dark. 50 ul of 0.16 M/L sulfuric acid was added to each well. The 450 nm OD value was obtained by Thermo Scientific™ Multiskan™ FC microplate reader, $EC_{50}$ value of IL-4R antibody binding to IL-4R was calculated.

2. ELISA Blocking Test:

In this test, by in vitro blocking experiment, the blocking of the binding of human IL-4R to human IL-4 by the selected anti-human IL-4R antibodies was detected. Specifically, the Fc-tagged IL-4R recombinant protein was coated onto a 96-well microtiter plate, the antibody that binds human IL-4R was added to fully bind to the epitope, and then IL-4 (Biolegend, Cat #574004) was added, biotin-conjugated anti-IL-4 antibody and NeutrAvidin®-HRP (Pierce, Cat #31001) were used to detect whether IL-4 can bind to IL-4R, $IC_{50}$ value was calculated for IL-4R antibody to block the IL-4/IL-4R binding.

Human IL-4R-Fc protein was coated onto 96-well microtiter plate, 100 μl per well at a concentration of 0.5 μg/ml, and incubated overnight at 4° C. The plate was washed with washing solution for three times, 250 μl per well. Each washing step was performed with shaking for 10 seconds to ensure sufficient washing. 200 μl/well blocking solution was added and incubated at room temperature for 2 hours. The plate was washed with washing solution for three times, 250 μl per well. Each washing step was performed with shaking for 10 seconds to ensure sufficient washing. 100 μl of anti-IL-4R antibody to be tested diluted with diluent was added to each well, and incubated at room temperature for 1 hour. The plate was washed with washing solution for three times, 250 μl per well. 100 μl of diluted IL-4 was added to each well and incubated at room temperature for 1 hour. The plate was washed with washing solution for three times. 100 μl diluted biotin-conjugated anti-IL-4 antibody was added to each well and incubated at room temperature for 1 hour. The plate was washed with washing solution for three times. HRP-labeled NeutrAvidin® (diluted at 1:5000 with diluent) was added and incubated at room temperature for 1 hour. The plate was washed with washing solution for three times, 250 μl per well. 100 μl TMB was added to each well and the reaction was maintained for 15 minutes in dark. 50 μl of 0.16 M/L sulfuric acid was added to each well. The 450 nm OD value was obtained by Thermo Scientific™ Multiskan™ FC microplate reader, $IC_{50}$ value was calculated for IL-4R antibody to block the binding of IL-4R to IL-4.

Example 3: Reporter Cell Activity Experiment of Antibodies that Bind to Human IL-4R HEK-Blue™ IL-4 cells were purchased from InvivoGen® (Cat #hkb-stat6). The cells were stably transfected with human IL-4R gene and STAT6-mediated SEAP genome. The SEAP secreted into the supernatant can be detected by SEAP substrate QUANTI-Blue™ to characterize the activation level of IL-4R signaling pathway.

In this experiment, the activation of HEK-Blue™ IL-4 cells was detected, and the in vitro cell activity of IL-4R antibody was evaluated according to $IC_{50}$. HEK-Blue™ IL-4 cells were cultivated in DMEM medium containing 10% FBS, 100 μg/ml Zeocin (InvivoGen®, Cat #ant-zn-05) and 10 μg/ml Blasticidin (InvivoGen®, Cat #ant-bl-05); the cells were sub-cultured for 2 to 3 times a week, at a ratio of 1:5 or 1:10. For sub-culturing, the medium was removed, and the cell layer was washed with 5 ml of 0.25% trypsin, then the trypsin was removed, the cells were placed in an incubator for 3 to 5 minutes, and fresh medium was added to resuspend the cells. 100 μL of cell suspension was added to 96-well cell culture plate, at a density of $5 \times 10^5$ cells/ml, the medium was DMEM containing 10% FBS, 100 μg/ml Zeocin and 30 ug/ml Blasticidin, and 100 μl sterile water was added around the 96-well plate. The culture plate was incubated in an incubator for 24 hours (37° C., 5% CO2). Once the cells adhered to the wall, 100 μl of the serially diluted antibody to be tested was added to each well. The culture plate was incubated in an incubator for 20-24 hours (37° C., 5% CO2). 20 μl of cell supernatant was transferred from each well to a new 96-well flat bottom plate, 180 μl QUANTI-Blue™ substrate solution was added, and the culture plate was incubated in an incubator in dark for 1-3 hours. The absorbance at 620 nm was measured with a microplate reader (Thermo Scientific™ Multiskan™ FC).

Example 4: Antibody that Binds to Human IL-4R Inhibits Proliferation of TF-1 Cell TF-1 cells (ATCCX CRL-2003™) are lymphoma cells that express IL-4R and are sensitive to cytokines such as IL-4/IL-13. IL-4 can stimulate TF-1 cells to proliferate in the absence of GM-CSF. The neutralizing activities of different IL-4R antibodies were compared in the experiment by adding neutralizing antibodies to block the pathway of IL-4 and to inhibit the proliferation of TF-1 cells. TF-1 cells were cultured in RPMI1640 medium containing 10% FBS, 2 ng/ml GM-CSF (R&D, Cat #215-GM-010); the cells were sub-cultured for 2 to 3 times a week at a ratio of 1:10. 100 μL of cell suspension was added to 96-well cell culture plate, at a density of $2 \times 10^5$ cells/ml, the medium was RPMI1640 medium containing 10% FBS, and 100 μl sterile water was added around the 96-well plate. 50 μl of serially diluted antibody to be tested and 50 μl of IL-4 (R&D, Cat #204-IL-050) at a final concentration of 0.7 ng/ml were added to each well, the culture plate was incubated in an incubator for 72 hours (37° C., 5% CO2). When the culture was finished, the cell proliferation was detected using CTG kit (Promega®, Cat #G7572).

Example 5: In Vitro Binding Affinity and Kinetic Experiments

Biacore™, GE instrument was used to determine the binding affinity of humanized antibody against human IL-4R to human IL-4R.

The human anti-capture antibody was covalently coupled to bio-sensing chip CM5 of the Biacore™ instrument (Biacore™ X100, GE) according to the method described in the instruction of the human anti-capture kit (Cat. #BR-1008-39, GE), thereby a certain amount of antibody to be tested was captured by affinity; a series concentration gradients of IL-4R antigens (IL-4R antigens purchased from Acrobiosystems, Cat #ILR-H5221) flowed through the surface of the chip, reaction signals were real-time detected using Biacore™ instruments (Biacore™ X100, GE) to obtain binding and dissociation curves. After the dissociation of each cycle was completed, the biochip was cleaned and regenerated with the regeneration solution provided inside the human anti-capture kit. The amino coupling kit used in the experiment was purchased from GE (Cat. #BR-1000-50, GE), and the buffer was HBS-EP+10×buffer solution (Cat. #BR-1006-69, GE) diluted with D.I. Water to 1×(pH 7.4).

The data obtained from the experiment was fitted against (1:1) Binding model using Biacore™ X100 evaluation software2.0 GE, and the affinity value was obtained.

Example 6: Sequence and Preparation of Antibodies

By ELISA binding experiment (ELISA binding of human IL-4R-his) and ELISA blocking experiment (ELISA blocking of hIL-4/IL-4R) in Example 2 above, test of inhibiting the activation of HEK293-Blue IL-4 cells stimulated by IL-4 in Example 3, and test of inhibiting the proliferation of TF-1 cells stimulated by IL-4 in Example 4, two monoclonal hybridoma cell lines showing the best in vitro activity were selected. The activity test results are shown in Table 2.

TABLE 2

The selected hybridoma cell lines with the best in vitro activity

| No. of mouse | hybridoma | ELISA(EC$_{50}$) (ng/ml) human IL-4R-his | ELISA(EC$_{50}$) (ng/ml) rhesus IL-4R-his | ELISA(EC$_{50}$) (ng/ml) mouse IL-4R-his | Blocking of hIL-4/IL-4R by ELISA (IC$_{50}$) (ng/ml) | blocking of the binding of HEK293-Blue IL-4 cell (to IL-4) (IC$_{50}$) (ng/ml) | Inhibiting the proliferation of TF-1 cells by IL-4 (IC$_{50}$) (ng/ml) |
|---|---|---|---|---|---|---|---|
| 11 | 25G7 | 3.319 | no binding | no binding | 8.132 | 0.9749 | 51.26 |
| 3 | 7B10 | 45.78 | no binding | no binding | 29.86 | 79.76 | 418.1 |
|  | Dupilumab | 27.62 | no binding | no binding | 52.08 | 5.069 | 102.2 |

The monoclonal hybridoma cell lines 25G7 and 7B10 with the best in vitro activity were selected, and the monoclonal antibody sequence was cloned therefrom. The process of cloning a sequence from hybridoma is as follows. Hybridoma cells at logarithmic growth phase were collected, RNA was extracted by TRIzol® (Invitrogen™, 15596-018) (following the kit instructions), reverse transcription was performed (PrimeScript™ Reverse Transcriptase, Takara, cat #2680A). The cDNA obtained by reverse transcription was amplified by PCR using mouse Ig-Primer Set (Novagen®, TB326 Rev. B0503), and then delivered to sequencing company for sequencing, and the obtained antibody sequence was analyzed.

The heavy chain and light chain variable region sequences of murine monoclonal antibody 25G7 are as follows:

25G7 HCVR (SEQ ID NO: 1)

EVQLVESGGGLVKPGGSLKLSCAASGFTFSDYGMHWVRQAPEKGLEWVA
FISSGSSIIYYADIVKGRSTISRDNAKNTLFLQMTSLRSEDTAMYYCTR
GNKRGFFDYWGQGTILTVSS;

25G7 LCVR (SEQ ID NO: 2)

QIVLTQSPALMSASPGEKVTMTCNASSSVSYMYWYQRKPRSSPKPWIYL
DTSNLASGVPVRFSGSGSGTSYSLTISSMEAEDAATYYCQQWRSNPPML
TFGSGTKLEVK;

The CDR sequences contained therein are shown in Table 3.

TABLE 3

CDR sequences of monoclonal antibody 25G7

| name | sequence | SEQ ID NO |
|---|---|---|
| HCDR1 | GFTFSDYGMH | SEQ ID NO: 3 |
| HCDR2 | FISSGSSIIYYADIVKG | SEQ ID NO: 4 |
| HCDR3 | GNKRGFFDY | SEQ ID NO: 5 |
| LCDR1 | NASSSVSYMY | SEQ ID NO: 6 |
| LCDR2 | LTSNLAS | SEQ ID NO: 7 |
| LCDR3 | QQWRSNPPMLT | SEQ ID NO: 8 |

The heavy chain and light chain variable region sequences of mouse monoclonal antibody 7B10 are as follows:

7B10 HCVR (SEQ ID NO: 9)

QVQLQQPGTELLKPGASVSLSCKASGYTFTSYWMHWVKQRPGQGLEWIG
LIHPNSDTTKFSENFKTRATLTIDKSSSTAYMKLSSLTSEDSAVYYCAK
SKIITTIVARHWYFDVWGTGTTVTVSS;

7B10 LCVR (SEQ ID NO: 10)

DIVLTQSPPSLAVSLGQRATISCKASQSVDYGGDSYMNWYQQKLGQPPK
VLIYAASNLESGIPARFSGSGSGTDFTLNIHPVEEEDVATYYCQHSNEN
PPTFGGGTKLEIK;

The CDR sequences contained therein are shown in Table 4.

TABLE 4

CDR sequences of monoclonal antibody 7B10

| name | sequence | SEQ ID NO |
|---|---|---|
| HCDR1 | GYTFTSYWMH | SEQ ID NO: 11 |
| HCDR2 | LIHPNSDTTKFSENFKT | SEQ ID NO: 12 |
| HCDR3 | SKIITTIVARHWYFDV | SEQ ID NO: 13 |
| LCDR1 | KASQSVDYGGDSYMN | SEQ ID NO: 14 |
| LCDR2 | AASNLES | SEQ ID NO: 15 |
| LCDR3 | QHSNENPPT | SEQ ID NO: 16 |

The obtained variable region sequence was linked to the human constant region sequence to obtain a human-mouse chimeric antibody sequence. Using molecular cloning technology, the chimeric antibody sequence was inserted into a corresponding expression vector. Using HEK293 cell expression system, human-mouse chimeric antibodies 25G7-C and 7B10-C can be obtained.

According to the method of Examples 2 to 5, the purified chimeric antibody was tested for in vitro activity. The data are shown in Table 5. The results showed that for antibody 25G7-C, both the blocking effect on IL-4 binding and the inhibitory effect on cell proliferation were significantly better than that of the reference antibody Dupilumab (synthesized according WHO Drug Information, Vol. 26, No. 4, 2012 synthesis).

TABLE 5

Detection of In vitro activity

| | human IL-4R-his ELISA binding (EC$_{50}$) (ng/ml) | rhesus IL-4R-his ELISA binding (EC$_{50}$) (ng/ml) | hIL-4/IL-4R ELISA Blocking (IC$_{50}$) (ng/ml) | blocking the binding of HEK293- Blue IL-4 cell (to IL-4) (IC$_{50}$) (ng/ml) | Inhibiting the proliferation of TF-1 cells by IL-4 (IC$_{50}$) (ng/ml) | K$_D$ (nM) (Biacore ™) |
|---|---|---|---|---|---|---|
| 25G7-C | 9.094 | no binding | 39.69 | 2.025 | 20.27 | 0.725 |
| 7B10-C | 11.83 | no binding | 162.3 | 9.034 | 46.43 | 0.278 |
| Dupilumab | 55.84 | no binding | 209.4 | 3.235 | 207.2 | 0.126 |

Example 7: Humanization Experiment of Mouse Antibody

The two strains (25G7 and 7B10) showing the strongest functional activity among the obtained murine antibodies were humanized. On the basis of the obtained typical structure of murine antibody VH/VLCDR, the heavy, light chain variable region sequences were aligned to antibody Germline database, to obtain a human germline template with high homology. Among them, the human germline light chain framework region is derived from human kappa light chain genes, preferably human germline light chain templates IGKV3-11*01 (SEQ ID NO: 22, for antibody 25G7) and IGKV2D-29*01 (SEQ ID NO: 24, for antibody 7B10). The human germline heavy chain framework region is derived from human heavy chain, preferably human germline heavy chain template IGHV3-48*01 (SEQ ID NO: 21, for antibody 25G7) and IGHV1-2*02 (SEQ ID NO: 23, for antibody 7B10).

Human germline template sequences are shown below.
Human germline heavy chain template IGHV3-48*01:

(SEQ ID NO: 21)
EVQLVESGGGLVQPGGSLRLSCAASGFTFSSYSMNWVRQAPGKGLEWVS
YISSSSSTIYYADSVKGRFTISRDNAKNSLYLQMNSLRAEDTAVYYCAR;

Human germline light chain template IGKV3-11*01:

(SEQ ID NO: 22)
EIVLTQSPATLSLSPGERATLSCRASQSVSSYLAWYQQKPGQAPRLLIY
DASNRATGIPARFSGSGSGTDFTLTISSLEPEDFAVYYCQQRSNWP;

Human germline heavy chain template IGHV1-2*02:

(SEQ ID NO: 23)
QVQLVQSGAEVKKPGASVKVSCKASGYTFTGYYMHWVRQAPGQGLEWMG
WINPNSGGTNYAQKFQGRVTMTRDTSISTAYMELSRLRSDDTAVYYCAR;

Human germline light chain template IGKV2D-29*01:

(SEQ ID NO: 24)
DIVMTQTPLSLSVTPGQPASISCKSSQSLLHSDGKTYLYWYLQKPGQPP

QLLIYEVSNRFSGVPDRFSGSGSGTDFTLKISRVEAEDVGVYYCMQSIQ

LP.

The CDR regions of the murine antibody were grafted onto the selected humanized template, to replace the humanized variable region which was then recombined with the IgG constant region. Then, based on the three-dimensional structure of the murine antibody, the embedded residues, the residues that directly interact with the CDR regions, and the residues that have an important impact on the conformation of VL and VH were back-mutated to obtain a series of humanized molecules.

Among them, Hu7B10-VH-a, hu7B10-VH-b, and hu7B10-VH-c were modified for pharmaceutical purpose, and the first position of the heavy chain human germline template was changed from Q to E. hu25G7 was also subjected to modification for pharmaceutical purpose. The heavy chain variable region sequences of the two humanized antibodies are as shown in SEQ ID NOs: 25-27 and SEQ ID NOs: 31-33, respectively; the light chain variable region sequences are as shown in SEQ ID NOs: 28-30 and SEQ ID NOs: 34-36, respectively.

hu25G7-VH-a:

(SEQ ID NO: 25)
EVQLVESGGGLVQPGGSLRLSCAASGFTFSDYGMHWVRQAPGKGLEWVA
FISSGSSIIYYADIVKGRFTISRDNAKNSLYLQMNSLRAEDTAVYYCAR
GNKRGFFDYWGQGTLVTVSS;

hu25G7-VH-b:

(SEQ ID NO: 26)
EVQLVESGGGLVQPGGSLRLSCAASGFTFSDYGMHWVRQAPGKGLEWVA
FISSGSSIIYYADIVKGRFTISRDNAKNSLYLQMNSLRAEDTAVYYCTR
GNKRGFFDYWGQGTLVTVSS;

hu25G7-VH-c:

(SEQ ID NO: 27)
EVQLVESGGGLVQPGGSLRLSCAASGFTFSDYGMHWVRQAPGKGLEWVA
FISSGSSIIYYADIVKGRSTISRDNAKNSLYLQMNSLRAEDTAVYYCTR
GNKRGFFDYWGQGTLVTVSS;

hu25G7-VL-a:

(SEQ ID NO: 28)
EIVLTQSPATLSLSPGERATLSCNASSSVSYMYWYQQKPGQAPRLLIYL
TSNLASGIPARFSGSGSGTDFTLTISSLEPEDFAVYYCQQWRSNPPMLT
FGGGTKVEIK;

hu25G7-VL-b:

(SEQ ID NO: 29)
EIVLTQSPATLSLSPGERATLSCNASSSVSYMYWYQQKPGQAPRLLIYL
TSNLASGIPARFSGSGSGTDYTLTISSLEPEDFAVYYCQQWRSNPPMLT
FGGGTKVEIK;

hu25G7-VL-c:

(SEQ ID NO: 30)
EIVLTQSPATLSLSPGERATLSCNASSSVSYMYWYQQKPGQAPRPWIYL
TSNLASGIPARFSGSGSGTDYTLTISSLEPEDFAVYYCQQWRSNPPMLT
FGGGTKVEIK;

hu7B10-VH-a:

(SEQ ID NO: 31)
EVQLVQSGAEVKKPGASVKVSCKASGYTFTSYWMHWVRQAPGQGLEWMG
LIHPNSDTTKFSENFKTRVTMTRDTSISTAYMELSRLRSDDTAVYYCAR
SKIITTIVARHWYFDVWGQGTTVTVSS;

hu7B10-VH-b:
(SEQ ID NO: 32)
EVQLVQSGAEVKKPGASVKVSCKASGYTFTSYWMHWVRQAPGQGLEWMG
LIHPNSDTTKFSENFKTRVTMTIDTSISTAYMELSRLRSDDTAVYYCAK
SKIITTIVARHWYFDVWGQGTTVTVSS;

hu7B10-VH-c:
(SEQ ID NO: 33)
EVQLVQSGAEVKKPGASVKVSCKASGYTFTSYWMHWVRQAPGQGLEWMG
LIHPNSDTTKFSENFKTRVTLTIDKSISTAYMELSRLRSDDTAVYYCAK
SKIITTIVARHWYFDVWGQGTTVTVSS;

hu7B10-VL-a:
(SEQ ID NO: 34)
DIVMTQTPLSLSVTPGQPASISCKASQSVDYGGDSYMNWYLQKPGQPPQ
LLIYAASNLESGVPDRFSGSGSGTDFTLKISRVEAEDVGVYYCQHSNEN
PPTFGGGTKVEIK;

hu7B10-VL-b:
(SEQ ID NO: 35)
DIVLTQTPLSLSVTPGQPASISCKASQSVDYGGDSYMNWYLQKPGQPPQ
LLIYAASNLESGVPDRFSGSGSGTDFTLKISRVEAEDVGVYYCQHSNE
NPPTFGGGTKVEIK;

hu7B10-VL-c:
(SEQ ID NO: 36)
DIVMTQTPLSLSVTPGQPASISCKASQSVDYGGDSYMNWYLQKPGQPPQ
LLIYAASNLESGIPDRFSGSGSGTDFTLKISRVEAEDVGVYYCQHSNEN
PPTFGGGTKVEIK.

Selection of templates and back mutation design for hybridoma clone 25G7 are shown in Table 6.

TABLE 6

Selection of templates and back mutation design

| 25G7-VL | | 25G7-VH | |
|---|---|---|---|
| hu25G7-VL-a | grafted | hu25G7-VH-a | S49A |
| hu25G7-VL-b | F71Y | hu25G7-VH-b | S49A, A93T |
| hu25G7-VL-C | L46P, L47W, F71Y | hu25G7-VH-c | S49A, F67S, A93T |

Selection of templates and back mutation design for hybridoma clone 7B10 are shown in Table 7 below:

TABLE 7

Selection of templates and back mutation design

| 7B10-VL | | 7B10-VH | |
|---|---|---|---|
| hu7B10-VL-a | grafted | hu7B10-VH-a | grafted |
| hu7B10-VL-b | M4L | hu7B10-VH-b | R71I, R94K |
| hu7B10-VL-C | V58I | hu7B10-VH-c | M69L, R71I, T73K, R94K |

After small-scale expression test of the above light and heavy chain combinations and the comparison of the number of back mutations, the final humanized antibody hu25G7 (with VH-c heavy chain and VL-a light chain) and antibody hu7B10 molecule (with VH-b heavy chain and VL-b light chain) were comprehensively evaluated and selected; their respective complete light and heavy chain sequences are as shown in SEQ ID NOs: 17-20.

hu25G7 HC
(SEQ ID NO: 17)
EVQLVESGGGLVQPGGSLRLSCAASGFTFSDYGMHWVRQAPGKGLEWVA
FISSGSSIIYYADIVKGRSTISRDNAKNSLYLQMNSLRAEDTAVYYCTR
GNKRGFFDYWGQGTLVTVSSASTKGPSVFPLAPCSRSTSESTAALGCLV
KDYFPEPVTVSWNSGALTSGVHTFPAVLQSSGLYSLSSVVTVPSSSLGT
KTYTCNVDHKPSNTKVDKRVESKYGPPCPPCPAPEFLGGPSVFLFPPKP
KDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTT
PPVLDSDGSFFLYSRLTVDKSRWQEGNVFSCSVM HEALHNHYTQ KSL
SLSLGK;

hu25G7 LC
(SEQ ID NO: 18)
EIVLTQSPATLSLSPGERATLSCNASSSVSYMWYWYQQKPGQAPRLLIYL
TSNLASGIPARFSGSGSGTDFTLTISSLEPEDFAVYYCQQWRSNPPMLT
FGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSFNRGEC;

hu7B10 HC
(SEQ ID NO: 19)
EVQLVQSGAEVKKPGASVKVSCKASGYTFTSYWMHWVRQAPGQGLEWMG
LIHPNSDTTKFSENFKTRVTMTIDTSISTAYMELSRLRSDDTAVYYCAK
SKIITTIVARHWYFDVWGQGTTVTVSSASTKGPSVFPLAPSSKSTSGGT
AALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALH
NHYTQKSLSLSPGK;

hu7B10 LC
(SEQ ID NO: 20)
DIVLTQTPLSLSVTPGQPASISCKASQSVDYGGDSYMNWYLQKPGQPPQ
LLIYAASNLESGVPDRFSGSGSGTDFTLKISRVEAEDVGVYYCQHSNEN
PPTFGGGTKVEIKRTVAAPSVFIFPPSDEQLKSGTASVVCLLNNFYPRE
AKVQWKVDNALQSGNSQESVTEQDSKDSTYSLSSTLTLSKADYEKHKVY
ACEVTHQGLSSPVTKSFNRGEC.

The sequence of the humanized antibody was inserted into a corresponding expression vector by molecular cloning technology, and the corresponding humanized antibodies were obtained by expression in HEK293 cell expression system.

Example 8: Activity Data of Humanized Antibody

The humanized antibodies hu25G7 and hu7B10 were tested in vitro as described in Examples 2-5, and the test results are shown in Table 8. The results showed that both hu25G7 and hu7B10 bind to human IL-4R only, but not to rhesus IL-4R, indicating that both antibodies bind to epitope (s) of human IL-4R which is not homologous to rhesus IL-4R; and can specifically bind to human IL-4R. Both antibodies can block the IL-4/IL-4R binding and intracellular signaling pathways, resulting in the neutralization of IL-4 activation effect, and inhibition of the proliferation of TF-1 cells, wherein the blocking and inhibitory activity of hu25G7 is still significantly better than that of the reference antibody Dupilumab, whereas the affinity $K_D$ value is relatively lower.

TABLE 8

Detection of In vitro activity

| | human IL-4R-his ELISA binding (EC$_{50}$) (ng/ml) | rhesus IL-4R-his ELISA binding (EC$_{50}$) (ng/ml) | human IL-4/IL-4R ELISA Blocking (IC$_{50}$) (ng/ml) | blocking the binding of HEK293-Blue IL-4 cell (to IL-4) (IC$_{50}$) (ng/ml) | Inhibiting the proliferation of TF-1 cell by IL-4 (IC$_{50}$) (ng/ml) | K$_D$ (nM) (Biacore™) |
|---|---|---|---|---|---|---|
| hu25G7 | 3.413 | no binding | 23.6 | 0.9431 | 29.56 | 1.07 |
| hu7B10 | 12.010 | no binding | 75.3 | 6.8700 | 112.4 | 0.284 |
| Dupilumab | 42.560 | no binding | 178.7 | 0.6668 | 491.2 | 0.126 |

Example 9: Affinity Maturation Experiment of Humanized Antibody hu25G7

In order to obtain more effective anti-human IL-4R antibodies, the 25G7 antibody was subjected to affinity maturation through yeast display platform technology, and an affinity maturation yeast library targeting 6 CDRs was designed and prepared on the basis of the hu25G7 antibody, and degenerate primers were designed. The designed mutant amino acids were introduced into the hu25G7-scFv antibody library by PCR and homologous recombination; the size of each library was about 109. The constructed yeast library was verified by second-generation sequencing (GENEWIZ®) method to confirm the diversity of the library.

Biotin-labeled human IL-4R was used to select high-affinity antibodies from the hu25G7-scFv yeast library. After two rounds of MACS screening (streptomycin magnetic beads, Invitrogen™) and two rounds of FACS screening (BD FACSAria™ FUSION), yeast single clone was selected for monoclonal cultivation and expression induction. FACS (BD FACSCanto® II) was used to detect the binding of single yeast clone to human IL-4R, and single yeast clone with higher affinity than that of wild-type 25G7 antibody was selected for sequencing verification. After alignment and analysis of sequencing clones, the redundant sequence was removed, the non-redundant sequence was converted into a full-length human antibody molecule for expression in mammalian cells. The full-length antibody after affinity purification was tested for affinity using Biacore™ X-100 (GE Life Sciences), and candidate antibody molecules with higher affinity to human IL-4R were selected as follows. The affinity of these antibody molecules to human IL-4R is higher than that of wild-type hu25G7 antibody, wherein the affinity of hu25G7-A antibody molecule is comparative to that of Dupilumab, while the affinity of hu25G7-B molecule is significantly better than that of Dupilumab.

After affinity maturation, the light chain variable region sequence of the antibody hu25G7-A is as follows:

hu25G7-A LCVR (SEQ ID NO: 37)
EIVLTQSPATLSLSPGERATLSCRASSSVPYMYWYQQKPGQAPRLLIYL

TSNLASGIPARFSGSGSGTDFTLTISSLEPEDFAVYYCQQWRAYPPMLT

FGGGTKVEIK.

The CDR sequences contained therein are shown in Table 9.

TABLE 9

| | CDR sequences | |
|---|---|---|
| name | sequence | SEQ ID NO: |
| LCDR1 | RASSSVPYMY | SEQ ID NO: 38 |
| LCDR2 | LTSNLAS | SEQ ID NO: 7 |
| LCDR3 | QQWRAYPPMLT | SEQ ID NO: 40 |

The light chain variable region sequence of the antibody hu25G7-B is as follows:

hu25G7-B LCVR

EIVLTQSPATLSLSPGERATLSCRASPGVP-PLAWYQQKPGQAPRLLIYLASSRPSGI
PARFSGSGSGTDFTLTISSLEPED-FAVYYCQQWRSNPPMLTFGGGTKVEIK (SEQ ID NO: 41);

The CDR sequences contained therein are shown in Table 10.

TABLE 10

| | CDR sequences | |
|---|---|---|
| name | sequence | SEQ ID No. |
| LCDR1 | RASPGVPPLA | SEQ ID NO: 42 |
| LCDR2 | LASSRPS | SEQ ID NO: 39 |
| LCDR3 | QQWRSNPPMLT | SEQ ID NO: 8 |

The above light chain variable region hu25G7-A LCVR was recombined with the hu25G7 light chain constant region to obtain the hu25G7-A antibody light chain; the above light chain variable region hu25G7-B LCVR was recombined with the hu25G7 light chain constant region to obtain the hu25G7-B antibody light chain.

The unstable amino acid residues in hu25G7-VH-c were optimized to enhance druggability, resulting in heavy chain variable region hu25G7-VH:

(SEQ ID NO: 43)
EVQLVESGGGLVQPGGSLRLSCAASGFTFSDYGMHWVRQAPGKGLEWVA

FISSGSSIIYYADIVKGRSTISRDNAKNTLYLQMNSLRAEDTAVYYCTR

GNKRGFFDYWGQGTLVTVSS.

The heavy chain variable region described above can be recombined with the hu25G7 heavy chain constant region, resulting in the hu25G7-A/hu25G7-B antibody heavy chain.

The hu25G7-A and hu25G7-B full length heavy chain sequences are shown in SEQ ID NO: 44.

hu25G7 HC
(SEQ ID NO: 44)
EVQLVESGGGLVQPGGSLRLSCAASGFTFSDYGMHWVRQAPGKGLEWVA

FISSGSSIIYYADIVKGRSTISRDNAKNTLYLQMNSLRAEDTAVYYCTR

GNKRGFFDYWGQGTLVTVSSASTKGPSVFPLAPCSRSTSESTAALGCLV

KDYFPEPVTVSWNSGALTSGVHTFPAVLQSSGLYSLSSVVTVPSSSLGT

KTYTCNVDHKPSNTKVDKRVESKYGPPCPPCPAPEFLGGPSVFLFPPKP

KDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSL

SLGK;

Each of full length light chain sequences is shown in SEQ ID NOs: 45-46.

hu25G7-A LC
(SEQ ID NO: 45)
EIVLTQSPATLSLSPGERATLSCRASSSVPYMYWYQQKPGQAPRLLIYL
TSNLASGIPARFSGSGSGTDFTLTISSLEPEDFAVYYCQQWRAYPPMLT
FGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSFNRGEC;

hu25G7-B LC
(SEQ ID NO: 46)
EIVLTQSPATLSLSPGERATLSCRASPGVPPLAWYQQKPGQAPRLLIYL
ASSRPSGIPARFSGSGSGTDFTLTISSLEPEDFAVYYCQQWRSNPPMLT
FGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSENRGEC.

Example 10: Affinity Maturation Activity Data of Humanized Antibody

Two antibodies hu25G7-A and hu25G7-B were tested as described in Example 3 and Example 4; both antibodies of hu25G7-A and hu25G7-B can block the binding of IL-4/IL-4R, and the intracellular signaling pathway, leading to neutralization of activation effect of IL-4 and IL-13, and the inhibition of proliferation of TF-1 cells; the activity data are shown in Table 11.

TABLE 11

| | Comparison of activity data | | | | |
|---|---|---|---|---|---|
| antibody | human IL-4/IL-4R ELISA blocking ($IC_{50}$) (ng/ml) | blocking the binding of HEK293-Blue cells (with IL-4) ($IC_{50}$) (ng/ml) | blocking the binding of HEK293-Blue cells (with IL-13) ($IC_{50}$) (ng/ml) | Inhibiting the proliferation of TF-1 cells by IL-4 ($IC_{50}$) (ng/ml) | Inhibiting the proliferation of TF-1 cell by IL-13 ($IC_{50}$) (ng/ml) |
| hu25G7-A | 144.2 | 6.49 | 10.02 | 83.72 | 13.24 |
| hu25G7-B | 108.4 | 6.598 | 8.38 | 50.95 | 13.71 |
| Dupilumab | 156.3 | 12.48 | 14.75 | 100.9 | 18.10 |

In the experiment of inhibiting the proliferation of TF-1 cells caused by IL-13 stimulation, both hu25G7-A and hu25G7-B showed beneficial effects. The effect was repeatedly verified, and the results showed that under the same conditions, the inhibition ($IC_{50}$) value of hu25G7-A for IL-13-stimulated proliferation of TF-1 cells was 11.68, and the inhibition ($IC_{50}$) value of control Dupilumab for IL-13-stimulated proliferation of TF-1 cells was 22.85. When compared with Dupilumab, hu25G7 has a significantly improved effect in blocking the binding of IL-4, IL-13 to IL-4R, as well as the cell proliferation caused by such binding.

Example 11: Study on the Effect of Humanized Antibody on Mouse Dermatitis

To establish a mouse dermatitis model, IL-4/IL-4Rα transgenic mice (purchased from Cyagen Bioscience Biological Research Center (Taicang) Co., Ltd.) were used. 100 μL of 1.5% OXZ acetone olive oil solution (acetone:olive oil=4:1) was evenly applied to the abdomen of each mouse, from about 3 cm×3 cm, for sensitization. The day of sensitization was counted as D0 (Day 0). On Day 7, 20 μL of 1% OXZ acetone olive oil solution was evenly applied to both ears (both sides) of mice for challenge, and challenged once every 72 hours.

A total of 5 groups, including normal control group (only acetone olive oil solution was applied for sensitization and challenge), model control group, hu25G7-A, hu25G7-B and Dupilumab group, were set up in this experiment, with 3 to 5 mice per group. The administration dosage for administration group was 50 mg/kg, and the administration route was subcutaneous administration, twice per week (see Table 12 for detailed information). On day 27, the thickness of the ears was measured with vernier caliper, and the results are shown in FIG. 1.

TABLE 12

Dosing scheme for each group

| Group | Numbers of animals | administration route | administration dosage | administration frequency* |
|---|---|---|---|---|
| Normal control group | 3 (males) | S.C. | — | twice per week |
| Model control group | 5 (3 females + 2 males) | S.C. | — | twice per week |
| hu25G7-A | 5 (3 females + 2 males) | S.C. | 50 mg/kg | twice per week |
| hu25G7-B | 3 (2 females + 1 male) | S.C. | 50 mg/kg | twice per week |
| Dupilumab | 4 (2 females + 2 males) | S.C. | 50 mg/kg | twice per week |

The results showed that the mouse ears in model control group showed obvious pathological damage, and the ear thickness was significantly higher than that of normal control group. The ear thickness of mice in the hu25G7-A, hu25G7-B and Dupilumab groups was significantly lower than that of the model control group on day 27. That is, hu25G7-A, hu25G7-B and Dupilumab can be used to treat dermatitis, and hu25G7-B is more effective than Dupilumab.

What is claimed is:
1. An anti-interleukin 4 receptor (IL-4R) antibody or antigen-binding fragment thereof, wherein the anti-IL-4R antibody or the antigen-binding fragment thereof comprises:
(I) a heavy chain variable region, comprising HCDR1, HCDR2 and HCDR3 as shown in SEQ ID NO: 3, SEQ ID NO: 4 and SEQ ID NO: 5, respectively; and
a light chain variable region, comprising LCDR1, LCDR2 and LCDR3 as shown in SEQ ID NO: 6, SEQ ID NO: 7 and SEQ ID NO: 8, respectively;
(II) a heavy chain variable region, comprising HCDR1, HCDR2 and HCDR3 as shown in SEQ ID NO: 11, SEQ ID NO: 12 and SEQ ID NO: 13, respectively; and
a light chain variable region, comprising LCDR1, LCDR2 and LCDR3 as shown in SEQ ID NO: 14, SEQ ID NO: 15 and SEQ ID NO: 16, respectively;
(III) a heavy chain variable region, comprising HCDR1, HCDR2 and HCDR3 as shown in SEQ ID NO: 3, SEQ ID NO: 4 and SEQ ID NO: 5, respectively; and
a light chain variable region, comprising LCDR1, LCDR2 and LCDR3 as shown in SEQ ID NO: 38, SEQ ID NO: 7 and SEQ ID NO: 40, respectively; or
(IV) a heavy chain variable region, comprising HCDR1, HCDR2 and HCDR3 as shown in SEQ ID NO: 3, SEQ ID NO: 4 and SEQ ID NO: 5 respectively; and
a light chain variable region, comprising LCDR1, LCDR2 and LCDR3 as shown in SEQ ID NO: 42, SEQ ID NO: 39 and SEQ ID NO: 8, respectively.

2. The anti-IL-4R antibody or antigen-binding fragment thereof according to claim 1 further comprising:
a FR region sequence derived from a human germline light chain IGKV3-11*01 or IGKV2D-29*01; or
a back mutation sequence having at least 95% identity to a FR region derived from human germline light chain IGKV3-11*01 or IGKV2D-29*01
and/or further comprising
a FR region sequence derived from human germline heavy chain IGHV3-48*01 or IGHV1-2*02; or
a back mutation sequence having at least 95% identity to FR region derived from human germline heavy chain IGHV3-48*01 or IGHV1-2*02.

3. The anti-IL-4R antibody or antigen-binding fragment thereof according to claim 1, wherein the anti-IL-4R antibody or antigen-binding fragment thereof comprises:
a heavy chain variable region, comprising:
(I) a heavy chain variable region as shown in SEQ ID NO: 1 or a heavy chain variable region having at least 90% identity to SEQ ID NO: 1; and a light chain variable region as shown in SEQ ID NO: 2 or a light chain variable region having at least 90%, 95%, 98%, or 99% identity to SEQ ID NO: 2; or
(II) a heavy chain variable region as shown in SEQ ID NO: 9 or a heavy chain variable region having at least 90% identity to SEQ ID NO: 9; and a light chain variable region as shown in SEQ ID NO: 10 or a light chain variable region having at least 90% identity to SEQ ID NO: 10; or
(III) a heavy chain variable region as shown in SEQ ID NO: 43 or a heavy chain variable region having at least 90% identity to SEQ ID NO: 43; and a light chain variable region as shown in SEQ ID NO: 37 or a light chain variable region having at least 90%, 95%, 98%, or 99% identity to SEQ ID NO: 37; or
(IV) a heavy chain variable region as shown in SEQ ID NO: 43 or a heavy chain variable region having at least 90% identity to SEQ ID NO: 43; and a light chain variable region as shown in SEQ ID NO: 37 or a light chain variable region having at least 90%, 95%, 98%, or 99% identity to SEQ ID NO: 41.

4. The anti-IL-4R antibody or antigen-binding fragment thereof according to claim 1, wherein the anti-IL-4R antibody or antigen-binding fragment thereof comprises:
a heavy chain variable region as shown in SEQ ID NO: 1 and a light chain variable region as shown in SEQ ID NO: 2; or
a heavy chain variable region as shown in SEQ ID NO: 9 and a light chain variable region as shown in SEQ ID NO: 10; or
a heavy chain variable region as shown in SEQ ID NO: 43, and a light chain variable region as shown in SEQ ID NO: 37; or
a heavy chain variable region as shown in SEQ ID NO: 43, and a light chain variable region as shown in SEQ ID NO: 41.

5. The anti-IL-4R antibody or antigen-binding fragment thereof according to claim 1, wherein the anti-IL-4R antibody or antigen-binding fragment thereof comprises:
(I) a heavy chain variable region as shown in one of SEQ ID NOs: 25-27 or a heavy chain variable region having at least 90% identity to one of SEQ ID NOs: 25-27; and
a light chain variable region as shown in one of SEQ ID NOs: 28-30 or a light chain variable region having at least 90% identity to one of SEQ ID NOs: 28-30; or,
(II) a heavy chain variable region as shown in one of SEQ ID NOs: 31-33 or a heavy chain variable region having at least 90% identity to one of SEQ ID NOs: 31-33; and
and a light chain variable region as shown in one of SEQ ID NOs: 34-36 or a light chain variable region having at least 90% identity to one of SEQ ID NOs: 34-36.

6. The anti-IL-4R antibody or antigen-binding fragment thereof according to claim 1, wherein:
the heavy chain variable region of the antibody comprises heavy chain Fc region(s) of human IgG1, IgG2, IgG3 or IgG4 or variants thereof.

7. The anti-IL-4R antibody or antigen-binding fragment thereof according to claim 1, wherein:
the antigen-binding fragment is selected from the group consisting of a Fab, Fab'-SH, Fv, scFv, or (Fab')2 fragment.

8. The anti-IL-4R antibody or antigen-binding fragment thereof according to claim 1, wherein the anti-IL-4R antibody or antigen-binding fragment thereof comprises:
(I) a heavy chain as shown in SEQ ID NO: 17 or a heavy chain having at least 90% identity to SEQ ID NO: 17; and a light chain as shown in SEQ ID NO: 18 or a light chain having at least 90% identity to SEQ ID NO: 18; or
(II) a heavy chain as shown in SEQ ID NO: 19 or a heavy chain having at least 90% identity to SEQ ID NO: 19; and a light chain as shown in SEQ ID NO: 20 or a sequence having at least 90% identity to SEQ ID NO: 20; or
(III) a heavy chain as shown in SEQ ID NO: 44 or a heavy chain having at least 90% identity to SEQ ID NO: 44; and a light chain as shown in SEQ ID NO: 45 or a light chain having at least 90% identity to SEQ ID NO: 45; or
(IV) a heavy chain as shown in SEQ ID NO: 44 or a heavy chain having at least 90% identity to SEQ ID NO: 44; and a light chain as shown in SEQ ID NO: 46 or a light chain having at least 90% identity to SEQ ID NO: 46.

9. The anti-IL-4R antibody or antigen-binding fragment thereof according to claim 1, wherein the anti-IL-4R antibody or antigen-binding fragment thereof comprises any one selected from the group consisting of:
- a heavy chain as shown in SEQ ID NO: 17 and a light chain as shown in SEQ ID NO: 18; or
- a heavy chain as shown in SEQ ID NO: 19 and a light chain as shown in SEQ ID NO: 20; or
- a heavy chain as shown in SEQ ID NO: 44 and a light chain as shown in SEQ ID NO: 45; or
- a heavy chain as shown in SEQ ID NO: 44 and a light chain as shown in SEQ ID NO: 46.

10. The anti-IL-4R antibody or antigen-binding fragment thereof according to claim 1, wherein the anti-IL-4R antibody or antigen-binding fragment thereof is a murine antibody, chimeric antibody, human antibody, humanized antibody or fragment thereof.

11. A reagent, comprising the anti-IL-4R antibody or antigen-binding fragment thereof according to claim 1.

12. A pharmaceutical composition, comprising:
the anti-IL-4R antibody or antigen-binding fragment thereof according to claim 1; and
a pharmaceutically acceptable excipient, diluent or carrier.

13. A method for detecting or measuring IL-4R, the method comprising:
a step of contacting a sample with the anti-IL-4R antibody or antigen-binding fragment thereof according to claim 1.

14. A method for treating dermatitis, comprising:
administering an anti-IL-4R antibody or antigen-binding fragment thereof to a subject,
wherein the anti-IL-4R antibody or the antigen-binding fragment thereof comprises:
(I) a heavy chain variable region, comprising HCDR1, HCDR2 and HCDR3 as shown in SEQ ID NO: 3, SEQ ID NO: 4 and SEQ ID NO: 5, respectively; and
a light chain variable region, comprising LCDR1, LCDR2 and LCDR3 as shown in SEQ ID NO: 6, SEQ ID NO: 7 and SEQ ID NO: 8, respectively;
(II) a heavy chain variable region, comprising HCDR1, HCDR2 and HCDR3 as shown in SEQ ID NO: 11, SEQ ID NO: 12 and SEQ ID NO: 13, respectively; and
a light chain variable region, comprising LCDR1, LCDR2 and LCDR3 as shown in SEQ ID NO: 14, SEQ ID NO: 15 and SEQ ID NO: 16, respectively;
(III) a heavy chain variable region, comprising HCDR1, HCDR2 and HCDR3 as shown in SEQ ID NO: 3, SEQ ID NO: 4 and SEQ ID NO: 5, respectively; and
a light chain variable region, comprising LCDR1, LCDR2 and LCDR3 as shown in SEQ ID NO: 38, SEQ ID NO: 7 and SEQ ID NO: 40, respectively; or
(IV) a heavy chain variable region, comprising HCDR1, HCDR2 and HCDR3 as shown in SEQ ID NO: 3, SEQ ID NO: 4 and SEQ ID NO: 5 respectively; and
a light chain variable region, comprising LCDR1, LCDR2 and LCDR3 as shown in SEQ ID NO: 42, SEQ ID NO: 39 and SEQ ID NO: 8, respectively.

15. A polynucleotide, encoding the anti-IL-4R antibody or antigen-binding fragment thereof according to claim 1.

16. A vector comprising the polynucleotide of claim 15.

17. An isolated host cell, comprising the vector of claim 16, wherein the isolated host cell is selected from the group consisting of a bacteria, yeast, or mammalian cell.

18. A method for preparing an anti-IL-4R antibody or antigen-binding fragment thereof, comprising the following steps:
expressing the anti-IL-4R antibody or antigen-binding fragment thereof in the host cell of claim 17, and
isolating the anti-IL-4R antibody or antigen-binding fragment thereof from the host cell.

* * * * *

```
                        SEQUENCE LISTING

<160> NUMBER OF SEQ ID NOS: 46

<210> SEQ ID NO 1
<211> LENGTH: 118
<212> TYPE: PRT
<213> ORGANISM: Artificial Sequence
<220> FEATURE:
<221> NAME/KEY: DOMAIN
<222> LOCATION: (1)..(118)
<223> OTHER INFORMATION: murine mAb 25G7 heavy chain variable region

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Thr Arg Gly Asn Lys Arg Gly Phe Phe Asp Tyr Trp Gly Gln Gly Thr
            100                 105                 110

Ile Leu Thr Val Ser Ser
        115

<210> SEQ ID NO 2
<211> LENGTH: 108
<212> TYPE: PRT
<213> ORGANISM: Artificial Sequence
<220> FEATURE:
<221> NAME/KEY: DOMAIN
<222> LOCATION: (1)..(108)
<223> OTHER INFORMATION: murine mAb 25G7 light chain variable region

<400> SEQUENCE: 2

Gln Ile Val Leu Thr Gln Ser Pro Ala Leu Met Ser Ala Ser Pro Gly
1               5                   10                  15
```

```
Glu Lys Val Thr Met Thr Cys Asn Ala Ser Ser Ser Val Ser Tyr Met
            20                  25                  30

Tyr Trp Tyr Gln Arg Lys Pro Arg Ser Ser Pro Lys Pro Trp Ile Tyr
            35                  40                  45

Leu Thr Ser Asn Leu Ala Ser Gly Val Pro Val Arg Phe Ser Gly Ser
            50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Arg Ser Asn Pro Pro Met
                85                  90                  95

Leu Thr Phe Gly Ser Gly Thr Lys Leu Glu Val Lys
            100                 105

<210> SEQ ID NO 3
<211> LENGTH: 10
<212> TYPE: PRT
<213> ORGANISM: Artificial Sequence
<220> FEATURE:
<221> NAME/KEY: DOMAIN
<222> LOCATION: (1)..(10)
<223> OTHER INFORMATION: murine mAb 25G7 HCDR1

<400> SEQUENCE: 3

Gly Phe Thr Phe Ser Asp Tyr Gly Met His
1               5                   10

<210> SEQ ID NO 4
<211> LENGTH: 17
<212> TYPE: PRT
<213> ORGANISM: Artificial Sequence
<220> FEATURE:
<221> NAME/KEY: DOMAIN
<222> LOCATION: (1)..(17)
<223> OTHER INFORMATION: murine mAb 25G7 HCDR2

<400> SEQUENCE: 4

Phe Ile Ser Ser Gly Ser Ser Ile Ile Tyr Tyr Ala Asp Ile Val Lys
1               5                   10                  15

Gly

<210> SEQ ID NO 5
<211> LENGTH: 9
<212> TYPE: PRT
<213> ORGANISM: Artificial Sequence
<220> FEATURE:
<221> NAME/KEY: DOMAIN
<222> LOCATION: (1)..(9)
<223> OTHER INFORMATION: murine mAb 25G7 HCDR3

<400> SEQUENCE: 5

Gly Asn Lys Arg Gly Phe Phe Asp Tyr
1               5

<210> SEQ ID NO 6
<211> LENGTH: 10
<212> TYPE: PRT
<213> ORGANISM: Artificial Sequence
<220> FEATURE:
<221> NAME/KEY: DOMAIN
<222> LOCATION: (1)..(10)
<223> OTHER INFORMATION: murine mAb 25G7 LCDR1
```

```
<400> SEQUENCE: 6

Asn Ala Ser Ser Ser Val Ser Tyr Met Tyr
1               5                   10

<210> SEQ ID NO 7
<211> LENGTH: 7
<212> TYPE: PRT
<213> ORGANISM: Artificial Sequence
<220> FEATURE:
<221> NAME/KEY: DOMAIN
<222> LOCATION: (1)..(7)
<223> OTHER INFORMATION: murine mAb 25G7 LCDR2

<400> SEQUENCE: 7

Leu Thr Ser Asn Leu Ala Ser
1               5

<210> SEQ ID NO 8
<211> LENGTH: 11
<212> TYPE: PRT
<213> ORGANISM: Artificial Sequence
<220> FEATURE:
<221> NAME/KEY: DOMAIN
<222> LOCATION: (1)..(11)
<223> OTHER INFORMATION: murine mAb 25G7 LCDR3

<400> SEQUENCE: 8

Gln Gln Trp Arg Ser Asn Pro Pro Met Leu Thr
1               5                   10

<210> SEQ ID NO 9
<211> LENGTH: 125
<212> TYPE: PRT
<213> ORGANISM: Artificial Sequence
<220> FEATURE:
<221> NAME/KEY: DOMAIN
<222> LOCATION: (1)..(125)
<223> OTHER INFORMATION: murine mAb 7B10 heavy chain variable region

<400> SEQUENCE: 9

Gln Val Gln Leu Gln Gln Pro Gly Thr Glu Leu Leu Lys Pro Gly Ala
1               5                   10                  15

Ser Val Ser Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Leu Ile His Pro Asn Ser Asp Thr Thr Lys Phe Ser Glu Asn Phe
        50                  55                  60

Lys Thr Arg Ala Thr Leu Thr Ile Asp Lys Ser Ser Ser Thr Ala Tyr
65                  70                  75                  80

Met Lys Leu Ser Ser Leu Thr Ser Glu Asp Ser Ala Val Tyr Tyr Cys
                85                  90                  95

Ala Lys Ser Lys Ile Ile Thr Thr Ile Val Ala Arg His Trp Tyr Phe
                100                 105                 110

Asp Val Trp Gly Thr Gly Thr Thr Val Thr Val Ser Ser
            115                 120                 125

<210> SEQ ID NO 10
<211> LENGTH: 111
<212> TYPE: PRT
<213> ORGANISM: Artificial Sequence
<220> FEATURE:
<221> NAME/KEY: DOMAIN
```

```
<222> LOCATION: (1)..(111)
<223> OTHER INFORMATION: murine mAb 7B10 light chain variable region

<400> SEQUENCE: 10

Asp Ile Val Leu Thr Gln Ser Pro Ser Leu Ala Val Ser Leu Gly
1               5                   10                  15

Gln Arg Ala Thr Ile Ser Cys Lys Ala Ser Gln Ser Val Asp Tyr Gly
            20                  25                  30

Gly Asp Ser Tyr Met Asn Trp Tyr Gln Gln Lys Leu Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln His Ser Asn
                85                  90                  95

Glu Asn Pro Pro Thr Phe Gly Gly Gly Thr Lys Leu Glu Ile Lys
            100                 105                 110

<210> SEQ ID NO 11
<211> LENGTH: 10
<212> TYPE: PRT
<213> ORGANISM: Artificial Sequence
<220> FEATURE:
<221> NAME/KEY: DOMAIN
<222> LOCATION: (1)..(10)
<223> OTHER INFORMATION: murine mAb 7B10 HCDR1

<400> SEQUENCE: 11

Gly Tyr Thr Phe Thr Ser Tyr Trp Met His
1               5                   10

<210> SEQ ID NO 12
<211> LENGTH: 17
<212> TYPE: PRT
<213> ORGANISM: Artificial Sequence
<220> FEATURE:
<221> NAME/KEY: DOMAIN
<222> LOCATION: (1)..(17)
<223> OTHER INFORMATION: murine mAb 7B10 HCDR2

<400> SEQUENCE: 12

Leu Ile His Pro Asn Ser Asp Thr Thr Lys Phe Ser Glu Asn Phe Lys
1               5                   10                  15

Thr

<210> SEQ ID NO 13
<211> LENGTH: 16
<212> TYPE: PRT
<213> ORGANISM: Artificial Sequence
<220> FEATURE:
<221> NAME/KEY: DOMAIN
<222> LOCATION: (1)..(16)
<223> OTHER INFORMATION: murine mAb 7B10 HCDR3

<400> SEQUENCE: 13

Ser Lys Ile Ile Thr Thr Ile Val Ala Arg His Trp Tyr Phe Asp Val
1               5                   10                  15

<210> SEQ ID NO 14
<211> LENGTH: 15
<212> TYPE: PRT
<213> ORGANISM: Artificial Sequence
<220> FEATURE:
```

```
<221> NAME/KEY: DOMAIN
<222> LOCATION: (1)..(14)
<223> OTHER INFORMATION: murine mAb 7B10 LCDR1

<400> SEQUENCE: 14

Lys Ala Ser Gln Ser Val Asp Tyr Gly Gly Asp Ser Tyr Met Asn
1               5                   10                  15

<210> SEQ ID NO 15
<211> LENGTH: 7
<212> TYPE: PRT
<213> ORGANISM: Artificial Sequence
<220> FEATURE:
<221> NAME/KEY: DOMAIN
<222> LOCATION: (1)..(7)
<223> OTHER INFORMATION: murine mAb 7B10 LCDR2

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial Sequence
<220> FEATURE:
<221> NAME/KEY: DOMAIN
<222> LOCATION: (1)..(9)
<223> OTHER INFORMATION: murine mAb 7B10 LCDR3

<400> SEQUENCE: 16

Gln His Ser Asn Glu Asn Pro Pro Thr
1               5

<210> SEQ ID NO 17
<211> LENGTH: 445
<212> TYPE: PRT
<213> ORGANISM: Artificial Sequence
<220> FEATURE:
<221> NAME/KEY: CHAIN
<222> LOCATION: (1)..(445)
<223> OTHER INFORMATION: humanized antibody hu25G7 heavy chain

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 18
<211> LENGTH: 215
<212> TYPE: PRT
<213> ORGANISM: Artificial Sequence
<220> FEATURE:
<221> NAME/KEY: CHAIN
<222> LOCATION: (1)..(215)
<223> OTHER INFORMATION: humanized antibody hu25G7 light chain

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Asn Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45
```

-continued

Leu Thr Ser Asn Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ser Asn Pro Pro Met
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 19
<211> LENGTH: 455
<212> TYPE: PRT
<213> ORGANISM: Artificial Sequence
<220> FEATURE:
<221> NAME/KEY: CHAIN
<222> LOCATION: (1)..(455)
<223> OTHER INFORMATION: humanized antibody hu7B10 heavy chain

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Leu Ile His Pro Asn Ser Asp Thr Thr Lys Phe Ser Glu Asn Phe
    50                  55                  60

Lys Thr Arg Val Thr Met Thr Ile Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Lys Ile Ile Thr Thr Ile Val Ala Arg His Trp Tyr Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

-continued

```
Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 20
<211> LENGTH: 218
<212> TYPE: PRT
<213> ORGANISM: Artificial Sequence
<220> FEATURE:
<221> NAME/KEY: CHAIN
<222> LOCATION: (1)..(218)
<223> OTHER INFORMATION: humanized antibody hu7B10 light chain

<400> SEQUENCE: 20

Asp Ile Val Leu Thr Gln Thr Pro Leu Ser Leu Ser Val Thr Pro Gly
1               5                   10                  15

Gln Pro Ala Ser Ile Ser Cys Lys Ala Ser Gln Ser Val Asp Tyr Gly
            20                  25                  30

Gly Asp Ser Tyr Met Asn Trp Tyr Leu Gln Lys Pro Gly Gln Pro Pro
        35                  40                  45

Gln Leu Leu Ile Tyr Ala Ala Ser Asn Leu Glu Ser Gly Val Pro Asp
    50                  55                  60
```

```
Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln His Ser Asn
                 85                  90                  95

Glu Asn Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 98
<212> TYPE: PRT
<213> ORGANISM: Artificial Sequence
<220> FEATURE:
<221> NAME/KEY: DOMAIN
<222> LOCATION: (1)..(98)
<223> OTHER INFORMATION: human germline heavy chain template IGHV3-48*01

<400> SEQUENCE: 21

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 22
<211> LENGTH: 95
<212> TYPE: PRT
<213> ORGANISM: Artificial Sequence
<220> FEATURE:
<221> NAME/KEY: DOMAIN
<222> LOCATION: (1)..(95)
<223> OTHER INFORMATION: human germline light chain template IGKV3-11*01

<400> SEQUENCE: 22

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30
```

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 23
<211> LENGTH: 98
<212> TYPE: PRT
<213> ORGANISM: Artificial Sequence
<220> FEATURE:
<221> NAME/KEY: DOMAIN
<222> LOCATION: (1)..(98)
<223> OTHER INFORMATION: human germline heavy chain template IGHV1-2*02

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 24
<211> LENGTH: 100
<212> TYPE: PRT
<213> ORGANISM: Artificial Sequence
<220> FEATURE:
<221> NAME/KEY: DOMAIN
<222> LOCATION: (1)..(100)
<223> OTHER INFORMATION: human germline light chain template IGKV2D-
      29*01

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

```
<210> SEQ ID NO 25
<211> LENGTH: 118
<212> TYPE: PRT
<213> ORGANISM: Artificial Sequence
<220> FEATURE:
<221> NAME/KEY: DOMAIN
<222> LOCATION: (1)..(118)
<223> OTHER INFORMATION: hu25G7-VH-a

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Lys Arg Gly Phe Phe Asp Tyr Trp Gly Gln Gly Thr
            100                 105                 110

Leu Val Thr Val Ser Ser
        115

<210> SEQ ID NO 26
<211> LENGTH: 118
<212> TYPE: PRT
<213> ORGANISM: Artificial Sequence
<220> FEATURE:
<221> NAME/KEY: DOMAIN
<222> LOCATION: (1)..(118)
<223> OTHER INFORMATION: hu25G7-VH-b

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser
        115

<210> SEQ ID NO 27
<211> LENGTH: 118
<212> TYPE: PRT
<213> ORGANISM: Artificial Sequence
<220> FEATURE:
<221> NAME/KEY: DOMAIN
```

```
<222> LOCATION: (1)..(118)
<223> OTHER INFORMATION: hu25G7-VH-c

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser
        115

<210> SEQ ID NO 28
<211> LENGTH: 108
<212> TYPE: PRT
<213> ORGANISM: Artificial Sequence
<220> FEATURE:
<221> NAME/KEY: DOMAIN
<222> LOCATION: (1)..(108)
<223> OTHER INFORMATION: hu25G7-VL-a

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Asn Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Leu Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ser Asn Pro Pro Met
                85                  90                  95

Leu Thr Phe Gly Gly Gly Thr Lys Val Glu Ile Lys
            100                 105

<210> SEQ ID NO 29
<211> LENGTH: 108
<212> TYPE: PRT
<213> ORGANISM: Artificial Sequence
<220> FEATURE:
<221> NAME/KEY: DOMAIN
<222> LOCATION: (1)..(108)
<223> OTHER INFORMATION: hu25G7-VL-b

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Asn Ala Ser Ser Ser Val Ser Tyr Met
            20                  25                  30
```

Tyr Trp Tyr Gln Gln Lys Pro Gly Gln Ala Pro Arg Leu Leu Ile Tyr
            35                  40                  45

Leu Thr Ser Asn Leu Ala Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Arg Ser Asn Pro Pro Met
                85                  90                  95

Leu Thr Phe Gly Gly Gly Thr Lys Val Glu Ile Lys
            100                 105

<210> SEQ ID NO 30
<211> LENGTH: 108
<212> TYPE: PRT
<213> ORGANISM: Artificial Sequence
<220> FEATURE:
<221> NAME/KEY: DOMAIN
<222> LOCATION: (1)..(108)
<223> OTHER INFORMATION: hu25G7-VL-c

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Asn Ala Ser Ser Ser Val Ser Tyr Met
            20                  25                  30

Tyr Trp Tyr Gln Gln Lys Pro Gly Gln Ala Pro Arg Pro Trp Ile Tyr
            35                  40                  45

Leu Thr Ser Asn Leu Ala Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Arg Ser Asn Pro Pro Met
                85                  90                  95

Leu Thr Phe Gly Gly Gly Thr Lys Val Glu Ile Lys
            100                 105

<210> SEQ ID NO 31
<211> LENGTH: 125
<212> TYPE: PRT
<213> ORGANISM: Artificial Sequence
<220> FEATURE:
<221> NAME/KEY: DOMAIN
<222> LOCATION: (1)..(125)
<223> OTHER INFORMATION: hu7B10-VH-a

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Leu Ile His Pro Asn Ser Asp Thr Thr Lys Phe Ser Glu Asn Phe
        50                  55                  60

Lys Thr Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

```
Ala Arg Ser Lys Ile Ile Thr Thr Ile Val Ala Arg His Trp Tyr Phe
            100                 105                 110

Asp Val Trp Gly Gln Gly Thr Thr Val Thr Val Ser Ser
        115                 120                 125

<210> SEQ ID NO 32
<211> LENGTH: 125
<212> TYPE: PRT
<213> ORGANISM: Artificial Sequence
<220> FEATURE:
<221> NAME/KEY: DOMAIN
<222> LOCATION: (1)..(125)
<223> OTHER INFORMATION: hu7B10-VH-b

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Leu Ile His Pro Asn Ser Asp Thr Thr Lys Phe Ser Glu Asn Phe
    50                  55                  60

Lys Thr Arg Val Thr Met Thr Ile Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Lys Ile Ile Thr Thr Ile Val Ala Arg His Trp Tyr Phe
            100                 105                 110

Asp Val Trp Gly Gln Gly Thr Thr Val Thr Val Ser Ser
        115                 120                 125

<210> SEQ ID NO 33
<211> LENGTH: 125
<212> TYPE: PRT
<213> ORGANISM: Artificial Sequence
<220> FEATURE:
<221> NAME/KEY: DOMAIN
<222> LOCATION: (1)..(125)
<223> OTHER INFORMATION: hu7B10-VH-c

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Leu Ile His Pro Asn Ser Asp Thr Thr Lys Phe Ser Glu Asn Phe
    50                  55                  60

Lys Thr Arg Val Thr Leu Thr Ile Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Ser Lys Ile Ile Thr Thr Ile Val Ala Arg His Trp Tyr Phe
            100                 105                 110

Asp Val Trp Gly Gln Gly Thr Thr Val Thr Val Ser Ser
        115                 120                 125
```

```
<210> SEQ ID NO 34
<211> LENGTH: 111
<212> TYPE: PRT
<213> ORGANISM: Artificial Sequence
<220> FEATURE:
<221> NAME/KEY: DOMAIN
<222> LOCATION: (1)..(111)
<223> OTHER INFORMATION: hu7B10-VL-a

<400> SEQUENCE: 34
```

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Asp Tyr Gly
            20                  25                  30

Gly Asp Ser Tyr Met Asn Trp Tyr Leu Gln Lys Pro Gly Gln Pro Pro
        35                  40                  45

Gln Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Asn
                85                  90                  95

Glu Asn Pro Pro Thr Phe Gly Gly Gly Thr Lys Val Glu Ile Lys
            100                 105                 110

```
<210> SEQ ID NO 35
<211> LENGTH: 111
<212> TYPE: PRT
<213> ORGANISM: Artificial Sequence
<220> FEATURE:
<221> NAME/KEY: DOMAIN
<222> LOCATION: (1)..(111)
<223> OTHER INFORMATION: hu7B10-VL-b

<400> SEQUENCE: 35
```

Asp Ile Val Leu Thr Gln Thr Pro Leu Ser Leu Ser Val Thr Pro Gly
1               5                   10                  15

Gln Pro Ala Ser Ile Ser Cys Lys Ala Ser Gln Ser Val Asp Tyr Gly
            20                  25                  30

Gly Asp Ser Tyr Met Asn Trp Tyr Leu Gln Lys Pro Gly Gln Pro Pro
        35                  40                  45

Gln Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Asn
                85                  90                  95

Glu Asn Pro Pro Thr Phe Gly Gly Gly Thr Lys Val Glu Ile Lys
            100                 105                 110

```
<210> SEQ ID NO 36
<211> LENGTH: 111
<212> TYPE: PRT
<213> ORGANISM: Artificial Sequence
<220> FEATURE:
<221> NAME/KEY: DOMAIN
<222> LOCATION: (1)..(111)
<223> OTHER INFORMATION: hu7B10-VL-c

<400> SEQUENCE: 36
```

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Val Asp Tyr Gly
            20                  25                  30

Gly Asp Ser Tyr Met Asn Trp Tyr Leu Gln Lys Pro Gly Gln Pro Pro
            35                  40                  45

Gln Leu Leu Ile Tyr Ala Ala Ser Asn Leu Glu Ser Gly Ile Pro Asp
        50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Asn
                85                  90                  95

Glu Asn Pro Pro Thr Phe Gly Gly Gly Thr Lys Val Glu Ile Lys
            100                 105                 110

<210> SEQ ID NO 37
<211> LENGTH: 108
<212> TYPE: PRT
<213> ORGANISM: Artificial Sequence
<220> FEATURE:
<221> NAME/KEY: DOMAIN
<222> LOCATION: (1)..(108)
<223> OTHER INFORMATION: hu25G7-A light chain variable region

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Pro Tyr Met
            20                  25                  30

Tyr Trp Tyr Gln Gln Lys Pro Gly Gln Ala Pro Arg Leu Leu Ile Tyr
        35                  40                  45

Leu Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ala Tyr Pro Pro Met
                85                  90                  95

Leu Thr Phe Gly Gly Gly Thr Lys Val Glu Ile Lys
            100                 105

<210> SEQ ID NO 38
<211> LENGTH: 10
<212> TYPE: PRT
<213> ORGANISM: Artificial Sequence
<220> FEATURE:
<221> NAME/KEY: DOMAIN
<222> LOCATION: (1)..(10)
<223> OTHER INFORMATION: hu25G7-A LCDR1

<400> SEQUENCE: 38

Arg Ala Ser Ser Ser Val Pro Tyr Met Tyr
1               5                   10

<210> SEQ ID NO 39
<211> LENGTH: 7
<212> TYPE: PRT
<213> ORGANISM: Artificial Sequence
<220> FEATURE:
<221> NAME/KEY: DOMAIN
<222> LOCATION: (1)..(7)
<223> OTHER INFORMATION: hu25G7-B LCDR2

<400> SEQUENCE: 39

Leu Ala Ser Ser Arg Pro Ser
1               5

<210> SEQ ID NO 40
<211> LENGTH: 11
<212> TYPE: PRT
<213> ORGANISM: Artificial Sequence
<220> FEATURE:
<221> NAME/KEY: DOMAIN
<222> LOCATION: (1)..(11)
<223> OTHER INFORMATION: hu25G7-A LCDR3

<400> SEQUENCE: 40

Gln Gln Trp Arg Ala Tyr Pro Pro Met Leu Thr
1               5                   10

<210> SEQ ID NO 41
<211> LENGTH: 108
<212> TYPE: PRT
<213> ORGANISM: Artificial Sequence
<220> FEATURE:
<221> NAME/KEY: DOMAIN
<222> LOCATION: (1)..(108)
<223> OTHER INFORMATION: hu25G7-B light chain variable region

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Pro Gly Val Pro Pro Leu
            20                  25                  30

Ala Trp Tyr Gln Gln Lys Pro Gly Gln Ala Pro Arg Leu Leu Ile Tyr
        35                  40                  45

Leu Ala Ser Ser Arg Pro Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ser Asn Pro Pro Met
                85                  90                  95

Leu Thr Phe Gly Gly Gly Thr Lys Val Glu Ile Lys
            100                 105

<210> SEQ ID NO 42
<211> LENGTH: 10
<212> TYPE: PRT
<213> ORGANISM: Artificial Sequence
<220> FEATURE:
<221> NAME/KEY: DOMAIN
<222> LOCATION: (1)..(10)
<223> OTHER INFORMATION: hu25G7-B LCDR1

<400> SEQUENCE: 42

Arg Ala Ser Pro Gly Val Pro Pro Leu Ala
1               5                   10

<210> SEQ ID NO 43
<211> LENGTH: 118
<212> TYPE: PRT
<213> ORGANISM: Artificial Sequence
<220> FEATURE:
<221> NAME/KEY: DOMAIN
<222> LOCATION: (1)..(118)
<223> OTHER INFORMATION: hu25G7-VH-c optimized heavy chain variable
      region

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser
            115

<210> SEQ ID NO 44
<211> LENGTH: 445
<212> TYPE: PRT
<213> ORGANISM: Artificial Sequence
<220> FEATURE:
<221> NAME/KEY: CHAIN
<222> LOCATION: (1)..(445)
<223> OTHER INFORMATION: hu25G7-A and hu25G7-B heavy chain

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Phe Ile Ser Ser Gly Ser Ser Ile Ile Tyr Tyr Ala Asp Ile Val
    50                  55                  60

Lys Gly Arg Ser Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Asn Lys Arg Gly Phe Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
            210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 45
<211> LENGTH: 215
<212> TYPE: PRT
<213> ORGANISM: Artificial Sequence
<220> FEATURE:
<221> NAME/KEY: CHAIN
<222> LOCATION: (1)..(215)
<223> OTHER INFORMATION: hu25G7-A light chain

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Pro Tyr Met
            20                  25                  30

Tyr Trp Tyr Gln Gln Lys Pro Gly Gln Ala Pro Arg Leu Leu Ile Tyr
        35                  40                  45

Leu Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ala Tyr Pro Pro Met
                85                  90                  95

Leu Thr Phe Gly Gly Gly Thr Lys Val Glu Ile Lys Arg Thr Val Ala
            100                 105                 110

```
Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 46
<211> LENGTH: 215
<212> TYPE: PRT
<213> ORGANISM: Artificial Sequence
<220> FEATURE:
<221> NAME/KEY: CHAIN
<222> LOCATION: (1)..(215)
<223> OTHER INFORMATION: hu25G7-B light chain

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Pro Gly Val Pro Pro Leu
            20                  25                  30

Ala Trp Tyr Gln Gln Lys Pro Gly Gln Ala Pro Arg Leu Leu Ile Tyr
        35                  40                  45

Leu Ala Ser Ser Arg Pro Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ser Asn Pro Pro Met
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```